US010717967B2

(12) United States Patent
Yukari et al.

(10) Patent No.: US 10,717,967 B2
(45) Date of Patent: *Jul. 21, 2020

(54) DUCK ENTERITIS VIRUS AND THE USES THEREOF

(71) Applicant: CEVA SANTE ANIMALE, Libourne (FR)

(72) Inventors: Saeki Yukari, Ohta-Ku (JP); Shuji Saitoh, Yokohama (JP)

(73) Assignee: CEVA SANTE ANIMALE, Libourne (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/251,111

(22) Filed: Jan. 18, 2019

(65) Prior Publication Data

US 2019/0136209 A1    May 9, 2019

Related U.S. Application Data

(63) Continuation of application No. 15/740,824, filed as application No. PCT/EP2016/065132 on Jun. 29, 2016, now Pat. No. 10,202,582.

(30) Foreign Application Priority Data

Jun. 30, 2015 (EP) .................................... 15174515

(51) Int. Cl.
| | | |
|---|---|---|
| *C12N 7/00* | (2006.01) | |
| *A61K 39/245* | (2006.01) | |
| *C12N 7/04* | (2006.01) | |
| *A61K 39/00* | (2006.01) | |

(52) U.S. Cl.
CPC .............. *C12N 7/00* (2013.01); *A61K 39/245* (2013.01); *C12N 7/04* (2013.01); *A61K 2039/5252* (2013.01); *A61K 2039/54* (2013.01); *C12N 2710/16334* (2013.01); *C12N 2710/16343* (2013.01); *C12N 2710/16361* (2013.01); *C12N 2710/16362* (2013.01)

(58) Field of Classification Search
None
See application file for complete search history.

(56) References Cited

U.S. PATENT DOCUMENTS

| | | | |
|---|---|---|---|
| 6,033,670 A | 3/2000 | Bublot et al. | |
| 10,202,582 B2 * | 2/2019 | Yukari | ..................... C12N 7/00 |
| 2019/0151439 A1 | 5/2019 | Yukari | |

FOREIGN PATENT DOCUMENTS

| | | |
|---|---|---|
| FR | 2 757 061 | 6/1998 |
| WO | WO 2014/036735 | 3/2014 |

OTHER PUBLICATIONS

Shen et al. (Virology Journal. 2010; 7: 232).*
Aravind, S. et al. "Adaptation and growth kinetics study of an Indian isolate of virulent duck enteritis virus in Vero cells" *Microbial Pathogenesis*, Nov. 13, 2015, pp. 14-19, vol. 78.
Li, H. et al. "Comparative analysis of the genes UL1 through UL7 of the duck enteritis virus and other herpesviruses of the subfamily Alphaherpesvirinae" *Genetics and Molecular Biology*, 2009, pp. 121-128, vol. 32, No. 1.
Li, Y. et al. "Molecular characterization of the genome of duck enteritis virus" *Virology*, Sep. 1, 2009, pp. 151-161, vol. 391, No. 2.
Liu, J. et al. "A Duck Enteritis Virus-Vectored Bivalent Live Vaccine Provides Fast and Complete Protection against H5N1 Avian Influenza Virus Infection in Ducks" *Journal of Virology*, Nov. 2011, pp. 10989-10998, vol. 85, No. 21.
Liu, J. et al. "Recombinant duck enteritis virus works as a single-dose vaccine in broilers providing rapid protection against H5N1 influenza infection" *Antiviral Research*, 2013, pp. 329-333, vol. 97, No. 3.
Liu, X. et al. "Recombinant duck enteritis virus expressing the HA gene from goose H5 subtype avian influenza virus" *Vaccine*, Oct. 15, 2013, pp. 5953-5959, vol. 31, No. 50.
Pan, H.-Q. et al. "Molecular Characterization of the Duck Enteritis Virus UL4 Gene" *Virologica Sinica*, Jun. 2009, pp. 171-178, vol. 24, No. 3.
Wang, J. et al. "Complete genome sequence of virulent duck enteritis virus (DEV) strain 2085 and comparison with genome sequences of virulent and attenuated DEV strains" *Virus Research*, Jul. 5, 2011, pp. 316-325, vol. 160, No. 1.
Wu, Y. et al. "Comparative Genomic Analysis of Duck Enteritis Virus Strains" *Journal of Virology*, Dec. 2012, pp. 13841-13842, vol. 86, No. 24.
Yang, C. et al. "Biological properties of a duck enteritis virus attenuated via serial passaging in chick embryo fibroblasts" *Archives of Virology*, 2015, pp. 267-274, vol. 160, No. 1.
Zou, Z. et al. "Efficient strategy for constructing duck enteritis virus-based live attenuated vaccine against homologous and heterologous H5N1 avian influenza virus and duck enteritis virus infection" *Veterinary Research*, 2015, pp. 1-15, vol. 46, No. 42.
Written Opinion in International Application No. PCT/EP2016/065132, dated Sep. 2, 2016, pp. 1-8.
Markham, P. F. et al. "The organisation of the multigene family which encodes the major cell surface protein, pMGA, of Mycoplasma gallisepticum" *FEBS Letters*, 1994, pp. 347-352, vol. 352.
Papazisi, L. et al. "The complete genome sequence of the avian pathogen Mycoplasma gallisepticum strain $R_{low}$" *Microbiology*, 2003, pp. 2307-2316, vol. 149.
Bijlenga, G. et al. "Development and use of the H strain of avian infectious bronchitis virus from the Netherlands as a vaccine: a review" *Avian Pathology*, Dec. 2004, pp. 550-557, vol. 33, No. 6.
Steel, J. et al. "A combination in-ovo vaccine for avian influenza virus and Newcastle disease virus" *Vaccine*, 2008, pp. 522-531, vol. 26.

(Continued)

*Primary Examiner* — Shanon A. Foley
(74) *Attorney, Agent, or Firm* — Saliwanchik, Lloyd & Eisenschenk

(57) ABSTRACT

The present invention relates to DEV and the uses thereof. The invention is particularly suited to vaccinate poultry against avian pathogens.

14 Claims, 8 Drawing Sheets

Figure 1:
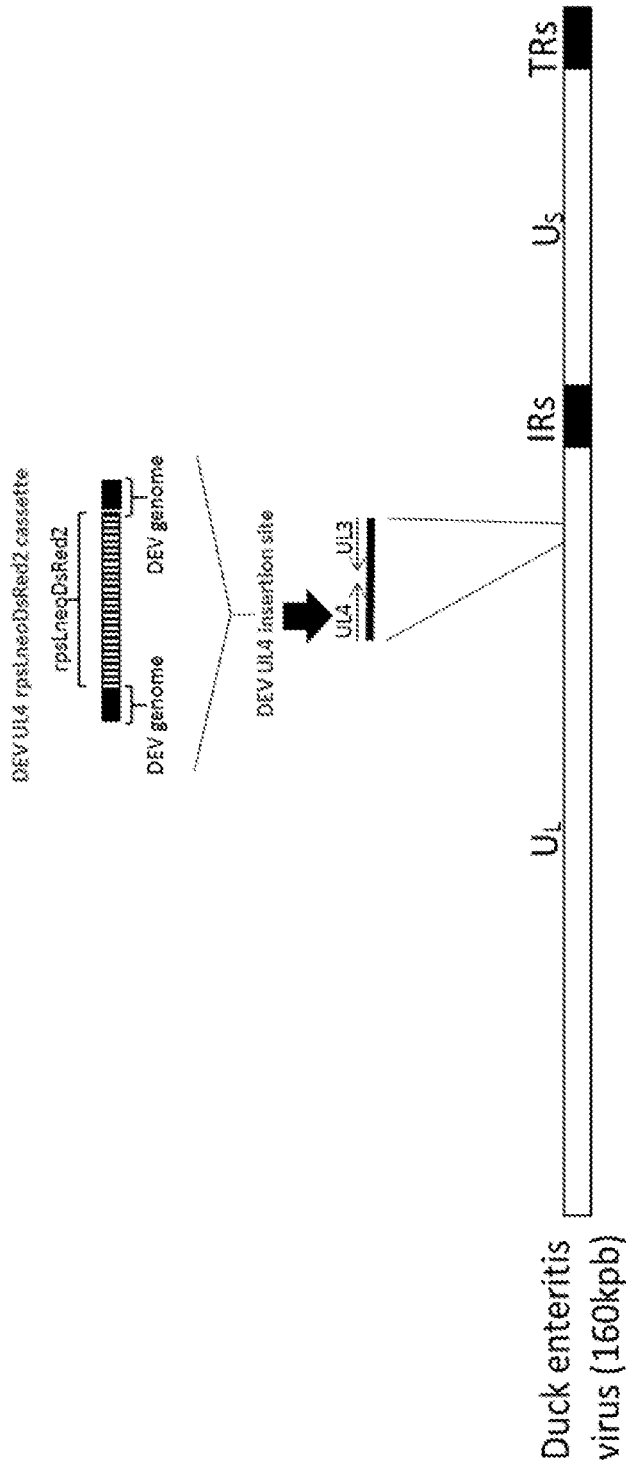

Specification includes a Sequence Listing.

(56) References Cited

OTHER PUBLICATIONS

Andoh, K. et al. "Turkey herpesvirus with an insertion in the UL3-4 region displays an appropriate balance between growth activity and antibody-eliciting capacity and is suitable for the establishment of a recombinant vaccine" *Archives of Virology*, 2017, pp. 931-941, vol. 162.

Morimoto, T. et al. "Identification of multiple sites suitable for insertion of foreign genes in herpes simplex virus genomes" *Microbiology and Immunology*, 2009, pp. 155-161, vol. 53.

\* cited by examiner

FIGURE 7

SEQUENCE LISTING

<160> NUMBER OF SEQ IDS NOS: 45

<210> SEQ ID NO 1
<211> LENGTH: 30
<212> TYPE: DNA
<213> ORGANISM: Artificial Sequence
<220> FEATURE:
<223> OTHER INFORMATION: Primer

<400> SEQUENCE: 1
ggcctggtga tgatggcggg atcgttgtat          30

<210> SEQ ID NO 2
<211> LENGTH: 30
<212> TYPE: DNA
<213> ORGANISM: Artificial Sequence
<220> FEATURE:

<223> OTHER INFORMATION: primer

<400> SEQUENCE: 2
ccatggtgct gcgctcagaa gaactcgtca                                    30

<210> SEQ ID NO 3
<211> LENGTH: 1319
<212> TYPE: DNA
<213> ORGANISM: Artificial Sequence
<220> FEATURE:
<223> OTHER INFORMATION: synthetic

<400> SEQUENCE: 3
ggcctggtga tgatggcggg atcgttgtat atttcttgac accttttcgg catcgcccta      60
aaattcggcg tcctcatatt gtgtgaggac gttttattac gtgtttacga agcaaaagct    120
aaaaccagga gctatttaat ggcaacagtt aaccagctgg tacgcaaacc acgtgctcgc    180
aaagttgcga aaagcaacgt gcctgcgctg aagcatgcc cgcaaaaacg tggcgtatgt     240
actcgtgtat atactaccac tcctaaaaaa ccgaactccg cgctgcgtaa agtatgccgt    300
gttcgtctga ctaacggttt cgaagtgact tcctacatcg gtggtgaagg tcacaacctg    360
caggagcact ccgtgatcct gatccgtggc ggtcgtgtta agacctcccc gggtgttcgt    420
taccacaccg tacgtggtgc gcttgactgc tccggcgtta agaccgtaa gcaggctcgt     480 tccaagtatg gcgtgaagcg tcctaaggct taaggaggac aatcatgatt gaacaagatg    540
gattgcacgc aggttctccg gccgcttggg tggagaggct attcggctat gactgggcac    600
aacagacaat cggctgctct gatgccgccg tgttccggct gtcagcgcag gggcgcccgg    660 ttcttttttgt caagaccgac ctgtccggtg ccctgaatga actgcaggac gaggcagcgc    720
ggctatcgtg gctggccacg acgggcgttc cttgcgcagc tgtgctcgac gttgtcactg    780
aagcgggaag ggactggctg ctattgggcg aagtgccggg gcaggatctc ctgtcatctc    840
accttgctcc tgccgagaaa gtatccatca tggctgatgc aatgcggcgg ctgcatacgc    900
ttgatccggc tacctgccca ttcgaccacc aagcgaaaca tcgcatcgag cgagcacgta    960
ctcggatgga agccggtctt gtcgatcagg atgatctgga cgaagagcat caggggctcg   1020
cgccagccga actgttcgcc aggctcaagg cgcgcatgcc cgacggcgag gatctcgtcg   1080
tgacccatgg cgatgcctgc ttgccgaata tcatggtgga aaatggccgc ttttctggat   1140
tcatcgactg tggccggctg ggtgtggcgg accgctatca ggacatagcg ttggctaccc   1200
gtgatattgc tgaagagctt ggcggcgaat gggctgaccg cttcctcgtg ctttacggta   1260
tcgccgctcc cgattcgcag cgcatcgcct tctatcgcct tcttgacgag ttcttctga     1319

<210> SEQ ID NO 4
<211> LENGTH: 30
<212> TYPE: DNA
<213> ORGANISM: Artificial Sequence
<220> FEATURE:
<223> OTHER INFORMATION: primer

<400> SEQUENCE: 4
acgagttctt ctgagcgcag caccatggcc                                    30

<210> SEQ ID NO 5
<211> LENGTH: 30
<212> TYPE: DNA
<213> ORGANISM: Artificial Sequence
<220> FEATURE:
<223> OTHER INFORMATION: Primer

```
<400> SEQUENCE: 5
tcggaggagg ccatccttaa gagctgtaat                                   30

<210> SEQ ID NO 6
<211> LENGTH: 30
<212> TYPE: DNA
<213> ORGANISM: Artificial Sequence
<220> FEATURE:
<223> OTHER INFORMATION: primer

<400> SEQUENCE: 6
tacagctctt aaggatggcc tcctccgaga                                   30

<210> SEQ ID NO 7
<211> LENGTH: 30
<212> TYPE: DNA
<213> ORGANISM: Artificial Sequence
<220> FEATURE:
<223> OTHER INFORMATION: primer

<400> SEQUENCE: 7
gcagtgaaaa aaatgcttta tttgtgaaat                                   30

<210> SEQ ID NO 8
<211> LENGTH: 70
<212> TYPE: DNA
<213> ORGANISM: Artificial Sequence
<220> FEATURE:
<223> OTHER INFORMATION: primer

<400> SEQUENCE: 8
atgcaatcgc atccggcaac gtttataact tacactctgg ggggtaccgg ggcctggtga   60
tgatggcggg                                                         70

<210> SEQ ID NO 9
<211> LENGTH: 70
<212> TYPE: DNA
<213> ORGANISM: Artificial Sequence
<220> FEATURE:
<223> OTHER INFORMATION: Primer

<400> SEQUENCE: 9
ttaaatgtct ataccgttca ctgcaattgg ctcctgagac gttccattgc gcagtgaaaa   60
aaatgcttta                                                         70

<210> SEQ ID NO 10
<211> LENGTH: 30
<212> TYPE: DNA
<213> ORGANISM: Artificial Sequence
<220> FEATURE:
<223> OTHER INFORMATION: primer

<400> SEQUENCE: 10
tgtttagcgt tatccgccca ctgtgtaaac                                   30

<210> SEQ ID NO 11
<211> LENGTH: 23
<212> TYPE: DNA
<213> ORGANISM: Artificial Sequence
<220> FEATURE:
<223> OTHER INFORMATION: primer

<400> SEQUENCE: 11
```

```
tcagaagaac tcgtcaagaa ggc                                          23

<210> SEQ ID NO 12
<211> LENGTH: 28
<212> TYPE: DNA
<213> ORGANISM: Artificial Sequence
<220> FEATURE:
<223> OTHER INFORMATION: primer

<400> SEQUENCE: 12
gggagtattc acaaataat aaacaaac                                      28

<210> SEQ ID NO 13
<211> LENGTH: 717
<212> TYPE: DNA
<213> ORGANISM: Duck Enteritis Virus

<400> SEQUENCE: 13
atgcaatcgc atccggcaac gtttataact tacactctgg ggggtaccgg tgcttcgcat    60
acgtggactg ttccagaata tgaacaagtg atctgttcgt gcgatggagg atcgagatct   120
gttctggtcg ggaacaagac acgctgtgac aaactccctc cgtgtaatgt tattattcaa   180
cgcggccctc ttgggactct attcgtcgta gatattgggg atgcaatata ttcctatatg   240
ctacgttgtg atctaaaaaa acaacaggtc ggtacattat cagcctcacc tggttcatta   300
tatgtagttc cgtttacatc atgtaccgta gtcggagtag atagctacat ccgcagtgac   360
tctagtggtg tattaacgat tgcatggtct cataatacag tgcatataac aataactgta   420
tatggtctgt cggaagagtc tcagcgcatg gcaagcgttt cggccatatc tactgtcggg   480
caagactatg aaaatcttca ggatatagcc aaccaagagc aaagtgaaga tttactatct   540
gctgcaataa aagaagctaa tattggtgtc gactacatat cagatagtga gtcgtcatct   600
agaacggtta tggacgactt actaacttct attcaagatg aatgcctaga gacggccgac   660
tgcttctgca atggaacgtc tcaggagcca attgcagtga acggtataga catttaa      717

<210> SEQ ID NO 14
<211> LENGTH: 26
<212> TYPE: DNA
<213> ORGANISM: Artificial Sequence
<220> FEATURE:
<223> OTHER INFORMATION: primer

<400> SEQUENCE: 14
gcgcatgcac tatagcgcgc tcacag                                       26

<210> SEQ ID NO 15
<211> LENGTH: 30
<212> TYPE: DNA
<213> ORGANISM: Artificial Sequence
<220> FEATURE:
<223> OTHER INFORMATION: primer

<400> SEQUENCE: 15
cagacctaaa ggttaggccg tctgtgaatg                                   30

<210> SEQ ID NO 16
<211> LENGTH: 30
<212> TYPE: DNA
<213> ORGANISM: Artificial Sequence
<220> FEATURE:
<223> OTHER INFORMATION: primer

<400> SEQUENCE: 16
```
cattcacaga cggcctaacc tttaggtctg                                    30

<210> SEQ ID NO 17
<211> LENGTH: 27
<212> TYPE: DNA
<213> ORGANISM: Artificial Sequence
<220> FEATURE:
<223> OTHER INFORMATION: primer

<400> SEQUENCE: 17
gcgaattccg caaactacac aagtccg                                       27

<210> SEQ ID NO 18
<211> LENGTH: 25
<212> TYPE: DNA
<213> ORGANISM: Artificial Sequence
<220> FEATURE:
<223> OTHER INFORMATION: primer

<400> SEQUENCE: 18
cggtcgacac tcccaggggt gaagc                                         25

<210> SEQ ID NO 19
<211> LENGTH: 30
<212> TYPE: DNA
<213> ORGANISM: Artificial Sequence
<220> FEATURE:
<223> OTHER INFORMATION: primer

<400> SEQUENCE: 19
cggccaataa ggccaagaat gcattcggcc                                    30

<210> SEQ ID NO 20
<211> LENGTH: 30
<212> TYPE: DNA
<213> ORGANISM: Artificial Sequence
<220> FEATURE:
<223> OTHER INFORMATION: primer

<400> SEQUENCE: 20
tggccttatt ggccgccgta tgaattgcgc                                    30

<210> SEQ ID NO 21
<211> LENGTH: 25
<212> TYPE: DNA
<213> ORGANISM: Artificial Sequence
<220> FEATURE:
<223> OTHER INFORMATION: primer

<400> SEQUENCE: 21
gcgagctcct gcaaccacag accgc                                         25

<210> SEQ ID NO 22
<211> LENGTH: 27
<212> TYPE: DNA
<213> ORGANISM: Artificial Sequence
<220> FEATURE:
<223> OTHER INFORMATION: primer

<400> SEQUENCE: 22
gacgctatac ccaatgacga tgaaaac                                       27

<210> SEQ ID NO 23
<211> LENGTH: 20
<212> TYPE: DNA

```
<213> ORGANISM: Artificial Sequence
<220> FEATURE:
<223> OTHER INFORMATION: primer

<400> SEQUENCE: 23
gagcaacttc gagctgatcc                                              20

<210> SEQ ID NO 24
<211> LENGTH: 22
<212> TYPE: DNA
<213> ORGANISM: Artificial Sequence
<220> FEATURE:
<223> OTHER INFORMATION: primer

<400> SEQUENCE: 24
gtactgcccg gccggtctaa tg                                           22

<210> SEQ ID NO 25
<211> LENGTH: 24
<212> TYPE: DNA
<213> ORGANISM: Artificial Sequence
<220> FEATURE:
<223> OTHER INFORMATION: primer

<400> SEQUENCE: 25
gccagggaat ccagggaaaa agac                                         24

<210> SEQ ID NO 26
<211> LENGTH: 25
<212> TYPE: DNA
<213> ORGANISM: Artificial Sequence
<220> FEATURE:
<223> OTHER INFORMATION: primer

<400> SEQUENCE: 26
gcgcatgcca attgtctaat tccag                                        25

<210> SEQ ID NO 27
<211> LENGTH: 30
<212> TYPE: DNA
<213> ORGANISM: Artificial Sequence
<220> FEATURE:
<223> OTHER INFORMATION: primer

<400> SEQUENCE: 27
cccggccaat aaggccacag aaaaagcgcg                                   30

<210> SEQ ID NO 28
<211> LENGTH: 29
<212> TYPE: DNA
<213> ORGANISM: Artificial Sequence
<220> FEATURE:
<223> OTHER INFORMATION: primer

<400> SEQUENCE: 28
ctgtggcctt attggccggg atctggaac                                    29

<210> SEQ ID NO 29
<211> LENGTH: 23
<212> TYPE: DNA
<213> ORGANISM: Artificial Sequence
<220> FEATURE:
<223> OTHER INFORMATION: primer

<400> SEQUENCE: 29
gcgaattcat gtgctacgcc cag                                          23
```

```
<210> SEQ ID NO 30
<211> LENGTH: 28
<212> TYPE: DNA
<213> ORGANISM: Artificial Sequence
<220> FEATURE:
<223> OTHER INFORMATION: primer

<400> SEQUENCE: 30
cggtcgacat agaacgcgct tcatctaa                                            28

<210> SEQ ID NO 31
<211> LENGTH: 30
<212> TYPE: DNA
<213> ORGANISM: Artificial Sequence
<220> FEATURE:
<223> OTHER INFORMATION: primer

<400> SEQUENCE: 31
tggccaataa ggccgtttat tgtttattat                                          30

<210> SEQ ID NO 32
<211> LENGTH: 30
<212> TYPE: DNA
<213> ORGANISM: Artificial Sequence
<220> FEATURE:
<223> OTHER INFORMATION: primer

<400> SEQUENCE: 32
cggccttatt ggccaatctg attcatccaa                                          30

<210> SEQ ID NO 33
<211> LENGTH: 30
<212> TYPE: DNA
<213> ORGANISM: Artificial Sequence
<220> FEATURE:
<223> OTHER INFORMATION: primer

<400> SEQUENCE: 33
gcgagctccg cctaatcaca atcggtattg                                          30

<210> SEQ ID NO 34
<211> LENGTH: 27
<212> TYPE: DNA
<213> ORGANISM: Artificial Sequence
<220> FEATURE:
<223> OTHER INFORMATION: primer

<400> SEQUENCE: 34
ccgcatgcgc aactatatat gtcggtc                                             27

<210> SEQ ID NO 35
<211> LENGTH: 30
<212> TYPE: DNA
<213> ORGANISM: Artificial Sequence
<220> FEATURE:
<223> OTHER INFORMATION: primer

<400> SEQUENCE: 35
gggccaataa ggcccaaaag tacattttgt                                          30

<210> SEQ ID NO 36
<211> LENGTH: 30
<212> TYPE: DNA
<213> ORGANISM: Artificial Sequence
<220> FEATURE:
```

<223> OTHER INFORMATION: primer

<400> SEQUENCE: 36
gggccttatt ggcccaattt atttactatt                                              30

<210> SEQ ID NO 37
<211> LENGTH: 28
<212> TYPE: DNA
<213> ORGANISM: Artificial Sequence
<220> FEATURE:
<223> OTHER INFORMATION: primer

<400> SEQUENCE: 37
gcgaattctg gatatgatat accgttgc                                                28

<210> SEQ ID NO 38
<211> LENGTH: 29
<212> TYPE: DNA
<213> ORGANISM: Artificial Sequence
<220> FEATURE:
<223> OTHER INFORMATION: primer

<400> SEQUENCE: 38
cttgttccag atcccacaga aaaagcgcg                                               29

<210> SEQ ID NO 39
<211> LENGTH: 29
<212> TYPE: DNA
<213> ORGANISM: Artificial Sequence
<220> FEATURE:
<223> OTHER INFORMATION: primer

<400> SEQUENCE: 39
cgcgcttttt ctgtgggatc tggaacaag                                               29

<210> SEQ ID NO 40
<211> LENGTH: 26
<212> TYPE: DNA
<213> ORGANISM: Artificial Sequence
<220> FEATURE:
<223> OTHER INFORMATION: primer

<400> SEQUENCE: 40
gcgcatgccc acccatagcc tattac                                                  26

<210> SEQ ID NO 41
<211> LENGTH: 80
<212> TYPE: DNA
<213> ORGANISM: Artificial Sequence
<220> FEATURE:
<223> OTHER INFORMATION: primer

<400> SEQUENCE: 41
tatgattgac tgtttgcctt tcattaacat ccaaatatat ttgtacatga ggtaataggc             60
tatgggtgcc ttattggcca                                                         80

<210> SEQ ID NO 42
<211> LENGTH: 80
<212> TYPE: DNA
<213> ORGANISM: Artificial Sequence
<220> FEATURE:
<223> OTHER INFORMATION: primer

<400> SEQUENCE: 42
aacagtcaat cataacaaaa acatttactt ttagtcatac tgatgtgaat taggccttat             60

```
tggccttcta tttttgaaac                                                  80

<210> SEQ ID NO 43
<211> LENGTH: 24
<212> TYPE: DNA
<213> ORGANISM: Artificial Sequence
<220> FEATURE:
<223> OTHER INFORMATION: primer

<400> SEQUENCE: 43
gcgaattcat gaccatggac atgc                                             24

<210> SEQ ID NO 44
<211> LENGTH: 29
<212> TYPE: DNA
<213> ORGANISM: Artificial Sequence
<220> FEATURE:
<223> OTHER INFORMATION: primer

<400> SEQUENCE: 44
gtgcgccata tagacgtaat tcacatcag                                        29

<210> SEQ ID NO 45
<211> LENGTH: 29
<212> TYPE: DNA
<213> ORGANISM: Artificial Sequence
<220> FEATURE:
<223> OTHER INFORMATION: primer

<400> SEQUENCE: 45
ctgatgtgaa ttacgtctat atggcgcac                                        29
```

DUCK ENTERITIS VIRUS AND THE USES THEREOF

This application is a continuation of U.S. application Ser. No. 15/740,824, filed Dec. 29, 2017, which is the U.S. national stage application of International Patent Application No. PCT/EP2016/065132, filed Jun. 29, 2016.

The Sequence Listing for this application is labeled "Seq-List.txt" which was created on Oct. 22, 2018, and is 11 KB. The entire content of the sequence listing is incorporated herein by reference in its entirety.

FIELD OF THE INVENTION

The present invention relates to novel viruses and the uses thereof. More particularly, the invention relates to novel Duck Enteritis Virus constructs and their use to express or deliver polypeptides of interest to animals, particularly poultry. The invention is particularly suited to vaccinate poultry against avian pathogens.

BACKGROUND OF THE INVENTION

Poultry meat and eggs are important food sources, whose consumption increases continually due to the growth of the human population and their great quality-price ratio. The recent epidemic of avian influenza focused the public opinion on poultry health as well as food safety and security, and poultry vaccine technology has become a worldwide concern.

Recombinant viruses expressing pathogen proteins are commonly used as poultry vaccines against targeted pathogens. Vaccines including such viruses induce expression of foreign pathogen proteins or fragments thereof within infected cells, which can subsequently induce a specific and protective humoral immunity as well as cell-mediated immunity.

In this regard, a number of viruses, in which a foreign gene derived from a pathogen has been integrated, have been developed to be used as viral-vectored vaccines. These viral vectors (or recombinant viruses) are based typically on avipox viruses, such as fowlpox (EP-A-0,517,292), herpes viruses, particularly HVT (e.g., WO-A-87/04463, U.S. Pat. Nos. 5,980,906, 5,853,733), Newcastle disease virus (NDV) or avian adenoviruses. These recombinant avian viruses display variable levels of protection, depending on the disease and/or animal.

For instance, because Poxviruses, NDV, and adenoviruses do not persist in chickens, they are not considered the best candidates for long duration of immunity in chicken. Recombinant HVT expressing antigens have shown advantages and are currently commercialized for vaccination in chicken (e.g., Vectormune® IBD, Vectormune® ND, or Vectormune® LT).

Considering the increasing number and diversity of pathogens and the continuous growth of poultry consumption, there is, however, a need for alternative vaccination strategies and/or systems that may be used to cause effective protective immunity in poultry. There is in particular a need for effective systems to procure immunity in very young animals (3 days or less) or in ovo.

In this regard, new viral serotypes have been explored, with the aim to find alternative compatible viral vectors to improve vaccination in animals, particularly in poultry, allowing stable protein expression and effective protection.

WO2014/0036735 discusses the possible use of Duck Enteritis Virus in chicken. DEV naturally infects ducks or geese but has no known tropism for chicken. This document suggests that a DEV construct may be administered to 1-week-old chicken by intramuscular injection. In this document, however, only late administration is reported.

By conducting further experiments with DEV, the inventors have, however, found that such virus is lethal when administered to young chicken (3 days or less) or in ovo. Surprisingly, although administration to chicken of a wild-type DEV (or a DEV construct containing all native genes as proposed in WO2014/0036735) one week after hatch appears well tolerated, administration of such a construct at day 1 post-hatch or in ovo causes a very massive death of the animals (i.e., between 80-100%). Even more surprisingly, the inventors have been able to modify the structure of the DEV to produce DEV constructs that may be used in poultry, including at very early stage (3 days or less) or in ovo, and that can cause substantial and early stage protein expression in vivo. Such viruses thus represent novel potent vectors for vaccinating poultry.

SUMMARY OF THE INVENTION

The invention provides novel viral constructs suitable to express genes or proteins in vivo in animals, particularly poultry, including at very early stage (i.e., at day 3 post-hatch or earlier, as well as in ovo). Particularly, the invention provides novel DEVs obtained by inactivation of the UL4 gene, and demonstrates that such DEVs are (i) attenuated in vivo, particularly in chicken, and (ii) are stable and capable of expressing foreign genes in a manner suitable for inducing protective immunity. Because such DEVs have no known natural tropism for e.g., chicken, the use of such DEV constructs for vaccinating chicken involves no risk of dissemination or contamination to non-vaccinated animals. Furthermore, chicken have no maternal antibodies or immunity against DEV and the viruses of the invention can be used to induce very early onset of immunity in vaccinated animals. Surprisingly, as indicated previously, while wild-type DEV is lethal in young chicken or in ovo, the DEVs of the invention are safe and can effectively express genes of interest in vivo. Such novel DEVs thus represent very potent vectors for vaccinating non-human animals, particularly poultry, and for conferring early protective immunity.

An object of the invention more particularly relates to a Duck Enteritis Virus (DEV), wherein said virus has an inactive UL4 gene. The invention indeed shows that by inactivating the UL4 gene, viable, stable and replicative DEVs can be obtained, and that such viruses may be used to create recombinant DEVs by insertion of foreign genetic material. The results further show that such foreign genetic material is highly expressed from such viruses upon cell infection, and that such expression remains stable over time. Moreover, and strikingly, while native DEV as well as many other deleted DEV constructs produced by the inventors were found pathogenic or lethal in young chicken (at day 3 post-hatch or earlier) and in ovo, inactivation of UL4 generates attenuated viruses which can be used safely to express proteins and antigens into young animals, including in ovo. Such finding was totally surprising and offers high advantages and utility to the present viruses.

A further object of the invention thus relates to a Duck Enteritis Virus (DEV), wherein said virus has an inactive UL4 gene and comprises a foreign nucleic acid.

According to particular embodiments, the UL4 gene is mutated, or deleted, or interrupted; and/or the foreign nucleic acid is located in the UL4 gene, in replacement of all or part of the UL4 gene sequence, and/or the foreign nucleic acid encodes an avian pathogen.

A further object of the invention is a nucleic acid molecule comprising the genome of a DEV having an inactive UL4 gene.

The invention further relates to a host cell comprising a DEV or a nucleic acid as defined above.

The invention also provides a method for producing or replicating a DEV as defined above, comprising infecting a competent cell with a nucleic acid molecule or with a DEV as defined above, and collecting the DEV.

The invention also relates to a method for making a recombinant DEV, comprising inserting a foreign nucleic acid into the UL4 gene sequence of a DEV, preferably in replacement of all or at least 20% of the UL4 gene sequence.

The invention also provides a composition comprising a DEV, a nucleic acid, or a host cell as defined above, a pharmaceutically or veterinary acceptable excipient or carrier and, optionally, an adjuvant.

The invention also provides a vaccine comprising a DEV, a nucleic acid, or a host cell as defined above, a pharmaceutically or veterinary acceptable excipient or carrier and, optionally, an adjuvant.

A further object of the invention relates to a composition, DEV, nucleic acid or host cell as defined above, for use to vaccinate or immunize avians, particularly poultry, more particularly chicken, more particularly young poultry (at Day 3 post-hatch or earlier or in ovo).

A further object of the invention relates to a composition, DEV, nucleic acid or host cell as defined above, for use to induce protective immunity in avians, particularly poultry, more particularly chicken, more particularly young poultry (at Day 3 post-hatch or earlier or in ovo).

The invention also relates to a method of vaccinating a non-human animal, particularly poultry, more particularly chicken, more particularly young poultry (at Day 3 post-hatch or earlier or in ovo), comprising administering to said non-human animal a composition, or virus as defined above.

A particular object of the invention is a method of vaccinating poultry comprising in ovo administration of a composition, or virus as defined above.

Another particular object of the invention is a method of vaccinating poultry comprising administration of a composition, or virus as defined above at Day 1 (i.e., within about 24 hours) post-hatch.

In a further aspect, the invention provides a method for inducing an immunogenic or protective response in a non-human animal against one or more avian pathogens comprising administering to said non-human animal, particularly poultry, more particularly chicken, more particularly young poultry (at Day 3 post-hatch or earlier or in ovo), a composition, vaccine or virus as defined above.

The viruses or compositions of the invention may be administered by any route. Preferably, they are administered in ovo or by subcutaneous (e.g., s.c.) injection 1 or 2 days post-hatch, to confer immunity very early.

The invention further provides a vaccination kit for immunizing an avian, which comprises the following components:

a. an effective amount of a composition as above, and
b. a means for administering said composition to said avian.

The invention may be used for expressing a polypeptide in any animal, preferably for the vaccination of an avian, and it is suitable for expressing one or several polypeptides or peptides, particularly immunogenic peptides of avian pathogens.

LEGEND TO THE FIGURES

FIG. 1 illustrates a schematic diagram of the Duck enteritis virus (DEV) genome and the location of the cloned region of recombinant DEV/rpsLneo-DsRed2 including the insertion site.

FIG. 2 shows a diagram of recombinant DEV/rpsLneo-DsRed2 genome, indicating locations of Junction 1, Junction 2, and Junction 3 amplified in PCR reactions to confirm the genome structure of the virus.

FIG. 3 illustrates a schematic diagram of the DEV genome and the location of the UL4 gene and cloned region of pUC18-KAPEVAC-UL4del.

FIG. 4 illustrates a schematic diagram of the DEV genome and the location of the UL26/UL27 insertion region, indicating locations of Junction 1, Junction 2, and Junction 3 amplified in PCR reactions to confirm the genome structure of the virus.

FIG. 5 illustrates a schematic diagram of the DEV genome and the location of the UL23 gene and cloned region of pUC18-KAPEVAC-UL23del-BacVP2 and pUC18-KAPEVAC-UL23del-Coa5VP2.

FIG. 6 illustrates a schematic diagram of the DEV genome and the location of the UL45/UL46 insertion region.

Figure 7:
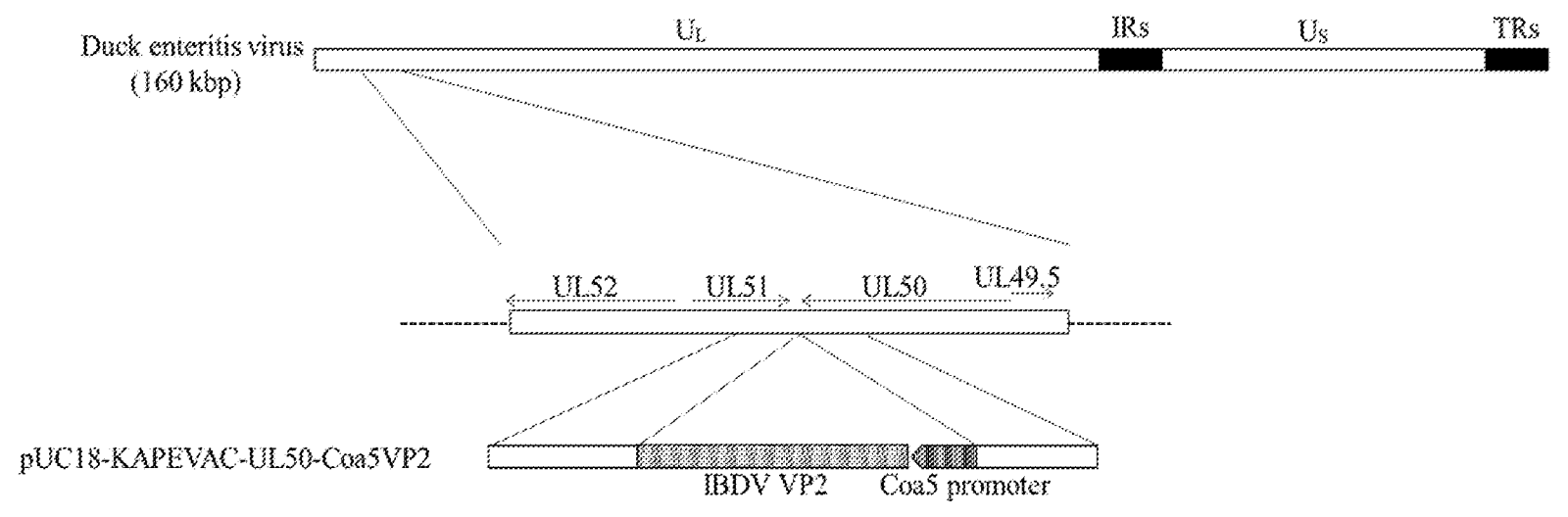

FIG. 7 illustrates a schematic diagram of the DEV genome and the location of the UL50/UL51 insertion region.

FIG. 8 illustrates a schematic diagram of the DEV genome and the location of the US7 region and cloned region of pUC18-KAPEVAC-US7-BacVP2.

DETAILED DESCRIPTION OF THE INVENTION

The present invention generally relates to attenuated DEVs, as well as to DEVs which comprise foreign gene sequence(s) located in particular insertion sites within the genome. The present invention also relates to compositions comprising such DEVs, as well as to the use thereof for vaccination of animals, particularly poultry, more particularly young poultry (at Day 3 post-hatch or earlier, or in ovo).

The present disclosure will be best understood by reference to the following definitions:

Definitions

The term “virus” designates in particular a viral particle comprising a nucleic acid molecule (e.g., a genome) encapsulated in a capsid or capsule. The term “virus” also designates a viral vector or an isolated viral genome.

The term “recombinant” designates a molecule which has been created, designed or modified using genetic technologies. In relation to a virus, the term “recombinant” more specifically designates a virus whose genome (or whose ancestor’s genome) has been modified by insertion or deletion of at least one nucleic acid sequence.

The term “foreign nucleic acid” in relation to a virus designates a nucleic acid which is not found naturally in the genome of the virus, or which is found naturally in said genome but in a different form or at a different position.

In the present description, the term “nucleic acid” or “nucleic acids” designates any nucleic acid molecule or sequence such as deoxyribonucleotide (DNA) or ribonucleotide (RNA), which may be e.g., single- or double-stranded. Nucleic acids may comprise an ORF or not. Nucleic acid molecules may be produced by techniques known per se in the art such as by artificial synthesis, recombinant technology, enzymatic technology, replication in host cells, or combinations thereof.

A "gene" designates a nucleic acid molecule or sequence which comprises an open reading frame encoding a product, such as a polypeptide (e.g., a peptide, protein, etc.) or an RNA.

The term "attenuated" as used herein refers to a virus which essentially does not cause illness in an animal model. An attenuated virus can typically replicate in a host without causing death thereof. An attenuated virus more particularly designates a virus which is not virulent in embryos when injected at a dose of $1 \times 10^3$ plaque forming unit (pfu)/egg. Most preferred attenuated viruses are safe at a dose of $1 \times 10^3$ pfu/egg in at least 70% injected eggs, more preferably in at least 80% injected eggs, even more preferably in at least 90%, 95% 97%, 98%, 99% or more. Attenuated viruses of the invention are also safe for injection post-hatch, including at Day 0 (i.e., between 0.1 and 48 hours post-hatch).

The term "avian" is intended to encompass all kinds of avians such as birds of the class of Ayes, i.e., vertebrate animals which are feathered, winged, bipedal, endothermic, and egg-laying. In the context of the invention, avians or avian species refer more particularly to birds with economical and/or agronomical interests, such as poultry, more preferably chickens and turkeys; or ornamental birds such as swans and psittacines.

The term "vaccine" as used herein designates an agent which may be used to cause, stimulate or amplify an immune response in an organism.

An "immune response" designates the development in a host of a cellular and/or antibody-mediated immune response to a composition or vaccine of interest. Usually, an "immune response" includes the production of antibodies, B cells, helper T cells, and/or cytotoxic T cells, directed specifically to an antigen or antigens included in the composition or vaccine of interest. Preferably, the immune response is protective such that resistance to new infection will be enhanced and/or the clinical severity of the disease reduced.

The term "in ovo" administration or injection generally means inoculation or injection in the embryo contained in an egg. In ovo injection is preferably conducted anytime between Day 5 and Day 1 before hatch.

Duck Enteritis Virus

Duck Enteritis Virus (DEV), also known as a duck viral enteritis virus (DVEV), naturally infects ducks and geese. The full nucleotide sequence of DEV has been determined and is available online (see for instance JQ673560). The viral genome contains about 162 Kb, encoding nearly 80 distinct proteins. Several serotypes and strains of DEV have been isolated, such as the Jansen strain, the CSC strain, the CHv strain, the VAC strain, and the 2085 strain.

DEV is poorly characterized and its use as a vector to express genes has not been deeply investigated. For instance, Liu et al (2013) and WO2014/0036735 have attempted to use a recombinant DEV for expressing genes into chicken. They have utilized a DEV construct wherein a nucleic acid has been cloned between the US7 and US8 genes of the viral genome, without altering native gene expression. Although it is reported that such a construct may be transferred by intramuscular injection into 1-week-old chicken, there is, however, no disclosure in this document or in any other prior art document of any possible use of DEV for in ovo vaccination of poultry, or for vaccination of young poultry, i.e., at Day 3 post-hatch or before, particularly at Day 1 or Day 2 post-hatch.

By conducting further experiments with DEV, the inventors surprisingly found that this virus is lethal when administered to young chicken (3 days or less) or in ovo. Surprisingly, although administration to chicken of a wild-type DEV (or a DEV construct containing all native genes as proposed in WO2014/0036735) one week after hatch appears well tolerated, administration of such a construct at day 1 post-hatch or in ovo causes a very massive death of the animals (i.e., between 80-100%), as reported in example 1.

Even more surprisingly, the inventors have been able to modify the structure of the DEV to produce DEV constructs that may be used in poultry, including at very early stage (3 days or less) or in ovo, and that can cause substantial and early stage protein expression in vivo. More particularly, the present inventors conducted further research with DEV and generated various recombinants with different gene deletions or alterations. The inventors have surprisingly discovered that one of these constructs was a stable, safe and potent DEV recombinant, while the others were essentially lethal in ovo. More particularly, by inactivation of the UL4 gene, recombinant DEVs can be obtained which are (i) attenuated in vivo, particularly in chicken, and (ii) stable and capable of expressing foreign genes in a manner suitable for inducing protective immunity. The invention indeed shows that by inactivating the UL4 gene, viable, stable and replicative DEVs can be obtained, and that such viruses may be used to insert foreign genetic material. The results further show that such foreign genetic material is highly expressed from such viruses upon cell infection, and that such expression remains stable over time. Moreover, and strikingly, while native DEV or other recombinant DEV are pathogenic or lethal in young chicken (below age of 3 days or in ovo), inactivation of UL4 generates attenuated DEVs which can be used safely to express proteins or antigens into young poultry and in ovo. Because DEV has no known natural tropism for e.g., chicken, the use of DEV constructs of the invention for vaccinating chicken involves no risk of dissemination or contamination to non-vaccinated animals. Furthermore, chicken have no maternal antibodies or immunity against DEV and the viruses of the invention can be used to induce very early onset of immunity in vaccinated animals.

An object of the invention thus relates to a Duck Enteritis Virus (DEV), wherein said virus has an inactive UL4 gene.

A further object of the invention relates to a Duck Enteritis Virus (DEV), wherein said virus has an inactive UL4 gene and contains a foreign nucleic acid.

Another object of the invention relates to a Duck Enteritis Virus (DEV), wherein said virus comprises has at least a first and a second inactive genes, wherein the first inactive gene is UL4 gene and the second inactive gene is selected from UL23 and US7 genes.

The DEV of the invention may be prepared from any DEV species or strain. A number of strains of DEV have been reported, which are available from public collections, such as the CSC strain (Genbank # JQ673560), the Jansen strain, the CHv strain (Genbank # JQ647509), the VAC strain (Genbank # EU082088), and the 2085 strain (Genbank # JF999965).

In a preferred embodiment, the DEV of the invention is derived or prepared from a parental strain selected from the Jansen strain or the CSC strain, or any DEV strain having at least 90% sequence identity to the Jansen strain or CSC strain, more preferably at least 95%, at least 96%, at least 97%, at least 98%, or at least 99%.

The invention shows that, by inactivating (i.e., rendering non-functional or deleting) the UL4 gene, it is possible to generate attenuated DEVs that are safe even when injected in ovo or in young poultry, and that can replicate and express proteins in poultry. The UL4 gene of DEV is predicted to encode a nuclear protein. However, the actual function of the UL4 gene of DEV remains unclear. Up to the present invention, the ability to generate UL4-defective DEV viruses was not known, and the ability of UL4-defective DEV viruses to replicate and express foreign genes, without being lethal in avians was totally unknown.

The UL4 gene is typically composed of 717 bp of a DEV genome. By reference to a CSC strain, the UL4 gene corresponds to nt112845 to nt113561 of the genome. The nucleotide sequence of a UL4 gene of a Jansen-type strain of DEV is represented in SEQ NO: 13. It is understood that the skilled artisan may easily identify the exact location of the UL4 gene in any DEV strain using the information contained in the present application and general common knowledge, or by sequence alignment.

Within the context of the invention, a DEV having an inactive UL4 gene designates a DEV that cannot express a functional UL4 protein. An inactive UL4 gene thus designates a mutated, a deleted, and/or an interrupted UL4 gene that cannot encode a wild-type UL4 protein.

Particular mutations are point mutations in the UL4 coding sequence that prevent expression of a full length UL4 protein. Such mutations may introduce a stop or non-sense codon in the sequence, or cause substitution of essential amino acid residue(s) in the encoded protein, resulting in an inactive protein.

In a particular DEV of the invention, at least 20% of the UL4 gene sequence is deleted, more preferably at least 30%, at least 40%, at least 50%, at least 60%, at least 70%, at least 80%, or at least 85%, up to 100%. In a preferred example, the DEV of the invention has a deletion of at least 400 bp of the UL4 gene sequence, more preferably at least 500 bp, at least 600 bp, or more.

In a specific embodiment, a DEV of the invention has a deletion spanning at least nt 200-500 of the UL4 gene sequence, more preferably at least nt100-600, even more preferably at least nt80-650. In a specific example, a DEV of the invention has a deletion of nt51 to nt667 (i.e., about 85%) of the UL4 gene sequence (e.g., DEV/UL4/rpsLneo-DsRed2).

As shown in the examples, DEV constructs having an inactive UL4 gene are stable, can be replicated in culture, and can be safely administered to poultry eggs or young poultry. Such viruses may thus be used to produce recombinant DEVs containing foreign nucleic acid material, particularly antigenic-coding genes, to express such genes in poultry.

In a particular embodiment, the invention thus relates to a Duck Enteritis Virus (DEV), wherein said virus has an inactive UL4 gene and comprises a foreign nucleic acid.

In a preferred embodiment, the foreign nucleic acid is located in the UL4 gene sequence of the DEV viral genome, either in addition to the existing UL4 gene sequence (thus rendering the gene inactive by interrupting the gene sequence), or in replacement of a deleted sequence of the UL4 gene, or in a mutated UL4 gene sequence.

In a preferred embodiment, the DEV of the invention has a deletion in the UL4 gene sequence, and contains a foreign nucleic acid located in place of the deleted nucleotides.

In another particular embodiment, the foreign nucleic acid is located in a cloning site of the DEV viral genome distinct from the UL4 gene sequence, either in addition to an existing gene sequence, or in replacement of a deleted sequence, or in a mutated gene sequence. Such additional insertion site may be selected from the UL44 gene, the UL27-UL26 intergenic region, the UL23 gene, the UL45-UL46 intergenic region, the UL50-UL51 intergenic region, the US4 gene, the US5 gene, the US7 gene, the US7-US8 intergenic region, or the US10 gene.

In the DEV of the invention, the foreign gene is generally under control of a transcriptional promoter. Preferably the promoter is cloned with the foreign gene. The promoter may be any natural or synthetic promoter, derived from cellular or viral genes. Examples of suitable promoters include, for instance, the chicken beta-actin (Bac) promoter or a derivative thereof such as Coa5, the Pec promoter, the Murine Cytomegalovirus (Mcmv) immediate-early (ie)1 promoter, the Human Cytomegalovirus promoter (Hcmv), the Simian virus (SV)40 promoter, and the Rous Sarcoma virus (RSV) promoter, or any fragments thereof which retain a promoter activity.

Furthermore, the DEV of the invention may comprise several foreign nucleic acids. In this regard, several foreign nucleic acids may be inserted in the UL4 region as described above, under the control of a single or several distinct promoters. Alternatively, the DEV may comprise a foreign nucleic acid inserted in UL4 and one or more foreign nucleic acids inserted in one or more distinct insertion sites. Such additional insertion sites may be selected from the UL44 gene, the UL27-UL26 intergenic region, the UL23 gene, the UL45-UL46 intergenic region, the UL50-UL51 intergenic region, the US4 gene, the US5 gene, the US7 gene, the US7-US8 intergenic region, or the US10 gene.

In this regard, in a particular embodiment, the invention relates to a Duck Enteritis Virus (DEV), wherein said virus has an inactive UL4 gene and an inactive UL44 gene. More particularly, the invention relates to a DEV, wherein said virus comprises a first foreign nucleic acid cloned into the UL4 gene, in replacement of at least 20% of said gene, and a second foreign nucleic acid cloned into the UL44 gene, in replacement of at least 20% of said gene. The UL44 gene is typically composed of 1296 bp of a DEV genome. By reference to a CSC strain, the UL44 gene corresponds to nt27419 to nt28714 of the genome. It is understood that the skilled artisan may easily identify the exact location of the UL44 gene in any DEV strain using the information contained in the present application and general common knowledge, or by sequence alignment. In a particular DEV of the invention, at least 20% of the UL44 gene sequence is deleted, more preferably at least 30%, at least 40%, at least 50%, at least 60%, at least 70%, at least 80%, at least 90%, up to 100%. In a preferred example, the DEV of the invention has a deletion of at least 500 bp of the UL44 gene sequence, more preferably at least 600, 700, 800, 900, 1000, or more. In a specific embodiment, a DEV of the invention has a deletion spanning at least nt 200-1000 of the UL44 gene sequence, more preferably at least nt100-1100, even more preferably at least nt100-1200. In a specific example, a DEV of the invention has a deletion of nt51 to nt1246 (i.e., more than 90%) of the UL44 gene sequence.

In another particular embodiment, the invention relates to a Duck Enteritis Virus (DEV), wherein said virus has an inactive UL4 gene and an inactive UL23 gene. Examples of such recombinant DEVs of the invention include JK015, JK022, JK023, JK024, and JK025. The invention shows that inactivation of these two genes generates DEVs which are highly attenuated, with about 95% survival rate upon in ovo administration. The results obtained also show that such attenuated viruses can replicate effectively in vitro and can express foreign gene sequences. More particularly, the invention relates to a DEV, wherein said virus comprises a first foreign nucleic acid cloned into the UL4 gene, in replacement of at least 20% of said gene, and a second foreign nucleic acid cloned into the UL23 gene, in replacement of at least 20% of said gene. The invention also relates to a DEV, wherein said virus comprises an inactive UL4 gene, and wherein said virus comprises a foreign nucleic acid cloned into the UL23 gene, in replacement of at least 20% of said gene. The invention also relates to a DEV, wherein said virus comprises an inactive UL4 gene and an inactive US7 gene, and wherein said virus comprises a foreign nucleic acid cloned into the UL23 gene, in replacement of at least 20% of said gene. The invention also relates to a DEV, wherein said virus comprises an inactive UL4 gene and an inactive UL23 gene, and wherein said virus comprises a foreign nucleic acid cloned into the UL26-27 intergenic region, or into the UL45-46 intergenic region, or into the UL50-51 intergenic region. The UL23 gene of DEV encodes thymidine kinase, which is believed to be involved in catalysis of nucleotide synthesis. Up to the present invention, the ability to generate UL23-defective DEV viruses was not known. The UL23 gene is typically composed of 1077 bp of a DEV genome. By reference to a CSC strain, the UL23 gene corresponds to nt77997 to nt79073 of the genome. It is understood that the skilled artisan may easily identify the exact location of the UL23 gene in any DEV strain using the information contained in the present application and general common knowledge, or by sequence alignment. In a particular DEV of the invention, at least 20% of the UL23 gene sequence is deleted, more preferably at least 30%, at least 40%, at least 50%, at least 60%, at least 70%, at least 80%, at least 90%, up to 100%. In a preferred example, the DEV of the invention has a deletion of at least 500 bp of the UL23 gene sequence, more preferable at least 600, 700, 800, 900, 1000, or more. In a specific embodiment, a DEV of the invention has a deletion spanning at least nt 200-900 of the UL23 gene sequence, more preferably at least nt100-1000, even more preferably at least nt80-1000. In a specific example, a DEV of the invention has a deletion of nt51 to nt1027 (i.e., about 90%) of the UL23 gene sequence.

In a further particular embodiment, the invention relates to a Duck Enteritis Virus (DEV), wherein said virus has an inactive UL4 gene and an inactive US4 gene. More particularly, the invention relates to a DEV, wherein said virus comprises a first foreign nucleic acid cloned into the UL4 gene, in replacement of at least 20% of said gene, and a second foreign nucleic acid cloned into the US4 gene, in replacement of at least 20% of said gene. The US4 gene of DEV encodes glycoprotein D, which is believed to be located on the viral envelope and the plasma membrane of infected cells. Up to the present invention, the ability to generate US4-defective DEV viruses was not known. The US4 gene is typically composed of 1380 bp of a DEV genome. By reference to a CSC strain, the US4 gene corresponds to nt141123 to nt142502 of the genome. It is understood that the skilled artisan may easily identify the exact location of the US4 gene in any DEV strain using the information contained in the present application and general common knowledge, or by sequence alignment. In a particular DEV of the invention, at least 20% of the US4 gene sequence is deleted, more preferably at least 30%, at least 40%, at least 50%, at least 60%, at least 70%, at least 80%, at least 90%, up to 100%. In a preferred example, the DEV of the invention has a deletion of at least 500 bp of the US4 gene sequence, more preferable at least 600, 700, 800, 900, 1000, or more. In a specific embodiment, a DEV of the invention has a deletion spanning at least nt 200-1000 of the US4 gene sequence, more preferably at least nt150-1150, even more preferably at least nt100-1300. In a specific example, a DEV of the invention has a deletion of nt51 to nt1330 (i.e., above 90%) of the US4 gene sequence.

In this regard, in a particular embodiment, the invention relates to a Duck Enteritis Virus (DEV), wherein said virus has an inactive UL4 gene and an inactive US5 gene. More particularly, the invention relates to a DEV, wherein said virus comprises a first foreign nucleic acid cloned into the UL4 gene, in replacement of at least 20% of said gene, and a second foreign nucleic acid cloned into the US5 gene, in replacement of at least 20% of said gene. The US5 gene of DEV encodes glycoprotein J, the function of which remains unknown. Up to the present invention, the ability to generate US5-defective DEV viruses was not known. The US5 gene is typically composed of 1620 bp of a DEV genome. In particular DEV strains, such as a 2085 strain and a Jansen strain, the US5 gene is shorter (about 1197 bp) as a result of mutations in the gene. By reference to a CSC strain, the US5 gene corresponds to nt142662 to nt144281 of the genome. It is understood that the skilled artisan may easily identify the exact location of the US5 gene in any DEV strain using the information contained in the present application and general common knowledge, or by sequence alignment. In a particular DEV of the invention, at least 20% of the US5 gene sequence is deleted, more preferably at least 30%, at least 40%, at least 50%, at least 60%, at least 70%, at least 80%, at least 90%, up to 100%. In a preferred example, the DEV of the invention has a deletion of at least 500 bp of the US5 gene sequence, more preferably at least 600, 700, 800, 900, 1000, or more. In a specific embodiment, a DEV of the invention has a deletion spanning at least nt 200-1000 of the US5 gene sequence, more preferably at least nt100-1100, even more preferably at least nt80-1120. In a specific example, a DEV of the invention produced from a Jansen strain has a deletion of nt51 to nt1147 (i.e., more than 90%) of the US5 gene sequence, and a DEV produced from a CSC strain has a deletion of nt51 to nt1570 of the US5 gene sequence.

In another particular embodiment, the invention relates to a Duck Enteritis Virus (DEV), wherein said virus has an inactive UL4 gene and an inactive US7 gene. Examples of such recombinant DEVs of the invention include JK016, JK025, JK026, JK027, and JK028. The invention shows that inactivation of these two genes generates DEVs which are highly attenuated, causing a 0% mortality upon in ovo administration. The results obtained also show that such attenuated viruses can replicate effectively in vitro and can express foreign gene sequences. More particularly, the invention relates to a DEV, wherein said virus comprises a first foreign nucleic acid cloned into the UL4 gene, in replacement of at least 20% of said gene, and a second foreign nucleic acid cloned into the US7 gene, in replacement of at least 20% of said gene. The invention also relates to a DEV, wherein said virus comprises an inactive UL4 gene, and wherein said virus comprises a foreign nucleic acid cloned into the US7 gene, in replacement of at least 20% of said gene. The invention also relates to a DEV, wherein said virus comprises an inactive UL4 gene and an inactive US7 gene, and wherein said virus comprises a foreign nucleic acid cloned into the UL23 gene, in replacement of at least 20% of said gene. The invention also relates to a DEV, wherein said virus comprises an inactive UL4 gene and an inactive US7 gene, and wherein said virus comprises a foreign nucleic acid cloned into the UL26-27 intergenic region, or into the UL45-46 intergenic region, or into the UL50-51 intergenic region. The US7 gene of DEV encodes glycoprotein I, which is believed to be involved in viral cell to cell spread. Up to the present invention, the ability to generate US7-defective DEV viruses was not known. The US7 gene is typically composed of 1116 bp of a DEV genome. By reference to a CSC strain, the US7 gene corresponds to nt145769 to nt146884 of the genome. It is understood that the skilled artisan may easily identify the exact location of the US7 gene in any DEV strain using the information contained in the present application and general common knowledge, or by sequence alignment. In a particular DEV of the invention, at least 20% of the US7 gene sequence is deleted, more preferably at least 30%, at least 40%, at least 50%, at least 60%, at least 70%, at least 80%, at least 90%, up to 100%. In a preferred example, the DEV of the invention has a deletion of at least 500 bp of the US7 gene sequence, more preferable at least 600, 700, 800, 900, 1000, or more. In a specific embodiment, a DEV of the invention has a deletion spanning at least nt 200-900 of the US7 gene sequence, more preferably at least nt100-1000, even more preferably at least nt80-1120. In a specific example, a DEV of the invention has a deletion of nt51 to nt1066 (i.e., more than 90%) of the US7 gene sequence.

In this regard, in a particular embodiment, the invention relates to a Duck Enteritis Virus (DEV), wherein said virus has an inactive UL4 gene and an inactive US10. More particularly, the invention relates to a DEV, wherein said virus comprises a first foreign nucleic acid cloned into the UL4 gene, in replacement of at least 20% of said gene, and a second foreign nucleic acid cloned into the US10 gene, in replacement of at least 20% of said gene. The US10 gene of DEV is predicted to encode a virion protein, the function of which remains unknown. Up to the present invention, the ability to generate US10-defective DEV viruses was not known. The US10 gene is typically composed of about 900 to 970 bp of a DEV genome, depending on the strain. By reference to a CSC strain, the US10 gene corresponds to nt136391 to nt137320 of the genome. It is understood that the skilled artisan may easily identify the exact location of the US10 gene in any DEV strain using the information contained in the present application and general common knowledge, or by sequence alignment. In a particular DEV of the invention, at least 20% of the US10 gene sequence is deleted, more preferably at least 30%, at least 40%, at least 50%, at least 60%, at least 70%, at least 80%, at least 90%, up to 100%. In a preferred example, the DEV of the invention has a deletion of at least 500 bp of the US10 gene sequence, more preferable at least 600, 700, or 800, or more. In a specific embodiment, a DEV of the invention has a deletion spanning at least nt 200-700 of the US10 gene sequence, more preferably at least nt100-800, even more preferably at least nt80-850. In a specific example, a DEV of the invention produced from a CSC strain has a deletion of nt51 to nt880 (i.e., more than 80%) of the US10 gene sequence, and a DEV produce from a VAC strain has a deletion of nt51 to nt847 of the US10 gene sequence.

The invention also relates to a DEV, wherein said virus comprises a first foreign nucleic acid cloned into the UL4 gene, in replacement of at least 20% of said gene, and a second foreign nucleic acid cloned in an intergenic region located between UL27 and UL26 genes. The invention also relates to a DEV, wherein said virus comprises an inactive UL4 gene, and wherein said virus comprises a foreign nucleic acid cloned in an intergenic region located between UL27 and UL26 genes. By reference to a CSC strain, the intergenic region located between UL27 and UL26 corresponds to nt72195 to nt72646 of the genome. Cloning may be performed at any position within such domain, more preferably between nt72300 and nt72500, furthermore preferably between nt72350 and nt72450. In a specific embodiment, cloning is performed between nt72431 and nt72432.

The invention also relates to a DEV, wherein said virus comprises a first foreign nucleic acid cloned into the UL4 gene, in replacement of at least 20% of said gene, and a second foreign nucleic acid cloned in an intergenic region located between US7 and US8 genes. Such an intergenic cloning site has been described in WO2014/0036735.

The invention also relates to a DEV, wherein said virus comprises an inactive UL4 gene, and wherein said virus comprises a foreign nucleic acid cloned in an intergenic region located between UL45 and UL46 genes, or between UL50 and UL51 genes. By reference to a CSC strain, the intergenic region located between UL45 and UL46 corresponds to nt25132 to nt25352 of the genome. Cloning may be performed at any position within such domain, more preferably between nt25200 and nt25300. In a specific embodiment, cloning is performed between nt25275 and nt25276. By reference to a CSC strain, the intergenic region located between UL50 and UL51 corresponds to nt15914 to nt16063 of the genome. Cloning may be performed at any position within such domain, more preferably between nt15970 and nt16010. In a specific embodiment, cloning is performed between nt15979 and nt15980.

Virus construction and cloning may be accomplished by techniques know per se in the art. Gene cloning and plasmid construction are well known to one person of ordinary skill in the art and may be essentially performed by standard molecular biology techniques (*Molecular Cloning*: A Laboratory Manual. 4th Edition, Cold Spring Harbor Laboratory, Cold Spring Harbor, N.Y., USA, 2012). Typically, the recombinant viruses may be prepared by homologous recombination between the viral genome and a construct (e.g., a homology plasmid) comprising the nucleic acid to be inserted, flanked by nucleotides from the insertion site to allow recombination. Cloning can be made with or without deletion of endogenous sequences. In a particular embodiment, the recombinant sequence is cloned in replacement of at least part of a sequence of the genome, such as at least 50 nucleotides or more. Such deletion increases the cloning capacity of the virus.

For construction, a sequence containing the targeted insertion region is typically first cloned into a suitable vector to produce a homology vector. Examples of vectors include plasmids, such as pBR322, pBR325, pBR327, pBR328, pUC18, pUC19, pUC7, pUC8, or pUC9; phages such as lambda phage and M13 phage; or cosmids such as pHC79. The target region sequence is integrated into the vector by conventional cloning methods. The target region sequence used is preferably of sufficient length so as to allow subsequent in vivo homologous recombination with a DEV viral genome. Preferably, the cloned target region sequence shall have at least approximately 100 nucleotides in length, typically above 300, such as between 500 and 2000 nucleotides. The foreign nucleic acid (which typically contains a gene and a promoter) is then inserted into the target region cloned in the vector. Insertion shall be made preferably in a manner that leaves a portion of sequence of the target region on each side of the cloned insert of a length sufficient to allow homologous recombination (e.g. of at least 50 nucleotides, preferably of at least 100 nucleotides). The foreign nucleic acid can be introduced into the cloned target region by classical techniques such as restriction enzyme and ligation procedures. If appropriate, mutation(s) may be introduced at a specific site of the target region to create a new cleavage site for a restriction enzyme. Conventional mutagenesis techniques well known by a person skilled in the art may be used for that purpose, such as e.g., in vitro mutagenesis or PCR. Homology vectors in which the foreign nucleic acid has been inserted into the target region may then be introduced into a DEV-infected cell or DEV genome-transfected cells using known techniques such as electroporation, calcium phosphate, lipofectin-based method, or the like. The recombinant viruses are thereby produced by recombination in said cells between the virus and the vector. The resulting recombinant virus may be selected genotypically or phenotypically using known techniques, e.g., by hybridization, sequencing, PCR or a functional assay to detect any product encoded by the foreign nucleic acid, as described in the examples. The selected recombinant virus can be cultured on a large scale in cell culture after which, recombinant viruses can be collected.

Foreign Gene

The DEV of the invention may contain any foreign nucleic acid, preferably any foreign gene. The foreign gene may encode any product of interest such as RNAs or biologically active and/or immunogenic (e.g., antigenic) proteins, polypeptides or peptides. In a preferred embodiment, the foreign gene encodes an antigen, even more preferably a peptide or polypeptide derived from an antigen of a pathogenic organism capable of causing an infection in an animal, particularly an avian. Examples of pathogens that cause infection in avian include viruses, bacteria, fungi, protozoa, etc. The immunogenic (poly)peptide may preferably be (derived from) a surface protein, a secreted protein, or a structural protein of said pathogen, or fragments thereof. The polypeptide can be derived from any source, e.g., viral, prokaryotic, eukaryotic or synthetic.

In a preferred embodiment, the foreign gene encodes an antigenic peptide of a bird pathogenic agent.

Specific examples of pathogenic agents include, without limitation, avian influenza virus, avian paramyxovirus type 1, also called Newcastle disease virus (NDV), avian metapneumovirus, Marek's disease virus, Gumboro disease virus, also called infectious bursal disease virus (IBDV), Infectious laryngotracheitis virus (ILTV), Infectious bronchitis virus (IBV), *Escherichia coli, Salmonella* species, *Pasteurella multocida, Riemerella anatipestifer, Ornithobacterium rhinotracheale, Mycoplasma gallisepticum, Mycoplasma synoviae, Mycoplasmas* microorganisms infecting avian species or coccidian.

Preferentially, the foreign gene encodes an antigen selected from the F protein of NDV, the HN protein of NDV, the VP2 protein of IBDV, the gB protein of ILTV, the 40K protein of *Mycoplasma gallisepticum*, or the surface protein hemagglutinin (HA) of the avian influenza virus, or immunogenic fragments thereof. Within the context of the invention, the term "fragment" of a protein designates preferably a fragment comprising at least 5 consecutive amino acid residues of said protein, even more preferably from 5-100. In a preferred embodiment, such a fragment comprises at least one epitope and/or is immunogenic in vivo, i.e., can cause production of antibodies that bind the full length protein.

Specific examples of immunogenic peptides include, for instance, a peptide comprising amino acid residues 1-453 of VP2, 1-469 of gB, or 1-540 of F.

Preferred DEVs

A preferred DEV of the invention comprises a deletion of the entire UL4 gene.

A particular DEV of the invention comprises a deletion of at least nt100-nt600 of the UL4 gene sequence, such as a deletion of nt51 to nt667 of a DEV UL4 genome.

Another preferred DEV of the invention comprises an inactive UL4 gene and an inactive UL23 gene.

Another preferred DEV of the invention comprises an inactive UL4 gene and an inactive US7 gene.

In a preferred DEV of the invention, the foreign nucleic acid encodes an avian antigen, more preferably a VP2, HN or F protein or an immunogenic fragment thereof.

Another preferred DEV of the invention comprises a deletion of at least nt100-nt600 of the UL4 gene sequence and at least one further deletion selected from:
- a deletion of at least nt100-nt1200 of the UL44 gene sequence,
- a deletion of at least nt100-nt1000 of the UL23 gene sequence,
- a deletion of at least nt100-nt1300 of the US4 gene sequence,
- a deletion of at least nt100-nt1100 of the US5 gene sequence,
- a deletion of at least nt100-nt1000 of the US7 gene sequence, and/or
- a deletion of at least nt100-nt800 of the US10 gene sequence, or combinations thereof.

Nucleic Acids

The invention also relates to a nucleic acid molecule comprising the genome of a DEV having an inactive UL4 gene. Such nucleic acid may be single- or double-stranded, DNA or RNA. In a particular embodiment, the nucleic acid is a DNA molecule containing the genome of a DEV as defined above.

The nucleic acid may be in free form, or in a vector such as a plasmid, BAC, and the like. The nucleic acid may be isolated, or contained in a host cell.

Cell Cultures

The recombinant viruses of the present invention may be propagated in any competent cell cultures. After required growth of the viruses is achieved, the cells may be detached from the wells using a scraper or with trypsin and the infected cells may be separated from the supernatant by centrifugation.

Examples of competent cells include CEF, embryonated egg, chicken kidney cell, and the like. The cells or viruses may be cultured in a culture medium such as Eagle's MEM, Leibowitz-L-15/McCoy 5A (1:1 mixture) culture medium at about 37° C. for 3 to 6 days. The infected cells are typically suspended in a culture medium containing 10% dimethyl sulfoxide (DMSO) and stored frozen under liquid nitrogen.

Compositions and Vaccines

The invention also relates to compositions, such as vaccines, which comprise one or more DEVs of the invention.

Compositions and vaccines of the invention may comprise the DEVs in a pharmaceutically or veterinary acceptable vehicle or excipient. The compositions and vaccines may, in addition or alternatively, comprise a suitable adjuvant.

The compositions and vaccines according to the present invention may comprise a suitable solvent, such as for example an aqueous buffer or a phosphate buffer. Preferably, the compositions and vaccines also comprise additives, such as a stabilizing agent, a preservative, a coloring agent, a surfactant, etc.

For instance, the compositions or vaccines of the present invention may be formulated with one or more further additives to maintain isotonicity, physiological pH and stability, for example, a buffer such as physiological saline (0.85%), phosphate-buffered saline (PBS), citrate buffers, Tris(hydroxymethyl aminomethane (TRIS), Tris-buffered saline and the like, or an antibiotic, for example, neomycin or streptomycin, etc.

In a particular embodiment, the composition of the invention comprises a preservative.

In another particular embodiment, the composition of the invention comprises a solubilizing agent.

In another particular embodiment, the composition of the invention comprises an adjuvant. Adjuvants may be obtained from any of a number of sources including various proteins and peptides derived from animals (e.g., hormones, cytokines, co-stimulatory factors), and novel nucleic acids derived from viruses and other sources (e.g., double stranded RNA, CpG), and the like which, alone or in combination(s), are sufficient to enhance the immune response.

The compositions of the invention may be liquid (solutions, suspensions, emulsions) or solid (powder, gel, paste, oil) and they may be formulated for any administration route. Preferably, they are formulated for injection, such as in ovo injection or for e.g., intravenous, subcutaneous, intramuscular, intraorbital, intraocular, intradermal, and/or intraperitoneal injection. Alternatively, they may be formulated for oral, ocular (e.g., by eye drop), intranasal, or oculo-nasal administration, e.g., using aerosol or spray.

Each vaccine dose may contain a suitable dose sufficient to elicit a protective immune response in avian species. Optimization of such dose is well known in the art. The amount of antigen per dose may be determined by known methods using antigen/anti-body reactions, for example by the ELISA method.

The vaccines of the invention can be administered as single doses or in repeated doses, depending on the vaccination protocol.

In a particular embodiment, the invention relates to a vaccine comprising a virus, nucleic acid or cell as defined above and a suitable excipient or adjuvant.

In a further particular embodiment, the invention relates to a vaccine comprising a liquid composition of a virus, nucleic acid or cell as defined above and a suitable excipient or adjuvant.

The present invention further relates to the use of the virus, composition, vaccine, nucleic acid or cell as described above for immunizing avian species, such as poultry, and to method of immunizing avian species by administering an immunologically effective amount of the virus, composition, vaccine, nucleic acid or cell as described above.

A further object of the invention relates to a composition, DEV, nucleic acid or host cell as defined above, for use to vaccinate or immunize avians, particularly poultry, more particularly chicken, more particularly young poultry (at Day 3 post-hatch or earlier) or in ovo.

A further object of the invention relates to a composition, vaccine, DEV, nucleic acid or host cell as defined above, for use to induce protective immunity in avians, particularly poultry, more particularly chicken, more particularly young poultry (at Day 3 post-hatch or earlier) or in ovo.

The invention also relates to a method of vaccinating a non-human animal, particularly poultry, more particularly chicken, more particularly young poultry (at Day 3 post-hatch or earlier or in ovo), comprising administering to said non-human animal a composition, vaccine, DEV, nucleic acid or host cell as defined above.

A particular object of the invention is a method of vaccinating poultry comprising in ovo administration of a composition, vaccine, DEV, nucleic acid or host cell as defined above.

Another particular object of the invention is a method of vaccinating poultry comprising administration of a composition, vaccine, DEV, nucleic acid or host cell as defined above, at Day 1 or at Day 2 post-hatch.

In a further aspect, the invention provides a method for inducing an immunogenic or protective response in a non-human animal against one or more avian pathogens, comprising administering to said non-human animal, particularly poultry, more particularly chicken, more particularly young poultry (at Day 3 post-hatch or earlier) or in ovo, a composition, vaccine, DEV, nucleic acid or host cell as defined above.

As indicated in the experimental section, the viruses of the invention are particularly advantageous for vaccinating young poultry (at Day 1, Day 2 or Day 3 post-hatch) or for in ovo vaccination. Indeed, the invention surprisingly shows that the viruses of the invention are safe upon such early administration, while native or wild-type DEV is lethal. Such early administration, combined with the early onset of immunity caused by these viruses, are particularly advantageous to induce early protective immunity, before poultry can be substantially exposed to pathogens.

In this regard, in a more general aspect, the invention also relates to a method for vaccinating or immunizing an avian, particularly poultry, more particularly chicken, the method comprising in ovo administration to said avian of an attenuated DEV encoding an antigen. The invention also relates to a method for expressing a foreign gene in an avian, particularly poultry, more particularly chicken, the method comprising in ovo administration to said avian of an attenuated DEV containing said foreign gene. The invention also relates to the use of an attenuated DEV containing a foreign gene for expressing said gene into an avian by in ovo administration of said DEV. The invention also relates to an attenuated DEV encoding an antigen, for use to induce an immune response or to vaccinate an avian by in ovo administration of said DEV. The DEV preferably comprises an inactive endogenous gene, rendering said DEV attenuated and well tolerated upon in ovo injection.

The present invention further relates to vaccination kits for immunizing avian species which comprises an effective amount of the multivalent vaccine as described above and a means for administering said components to said species. For example, such kit comprises an injection device filled with the vaccine according to the invention and instructions for intradermic, subcutaneous, intramuscular, or in ovo injection. Alternatively, the kit comprises a spray/aerosol or eye drop device filled with the vaccine according to the invention and instructions for oculo-nasal administration, oral or mucosal administration.

Further aspects and advantages of the invention will be disclosed in the following experimental section, which is illustrative of the claimed invention.

EXAMPLES

Example 1: Virulence of Wild-Type DEV in Eggs or Young Poultry

A clinical study was performed to investigate the pathogenicity or virulence of DEV at in chicken upon injection at different time schedule. More particularly, injection was performed in ovo (Day 3 before hatch), at Day 1 post-hatch, or at Day 4 post-hatch. DEV used was a wild-type DEV Jansen strain. The administered dose was either 100 or 1000 pfu/dose. As a control a PBS solution was administered in Group 1. Pathogenicity was assessed by measuring mortality each day after hatch.

The results are presented in the following table.

| Group | Vaccine | Dose pfu | Route | Day[1] | n | D0 | D1 | D2 | D3 | D4 | D5 | D6 | D7 | D8 | >D9[2] | % Mortality |
|---|---|---|---|---|---|---|---|---|---|---|---|---|---|---|---|---|
| 1 | PBS | — | in ovo | −3 | 17 | 0 | 0 | 0 | 0 | 0 | 0 | 0 | 0 | 0 | 2 | 12 |
| 2 | DEV | 100 | in ovo | −3 | 16 | 3 | 2 | 9 | 1 | 1 | — | — | — | — | — | 100 |
| 3 | DEV | 1000 | in ovo | −3 | 17 | 5 | 2 | 9 | 1 | — | — | — | — | — | — | 100 |
| 4 | DEV | 1000 | sc | 1 | 17 | 0 | 0 | 0 | 0 | 0 | 6 | 4 | 2 | 1 | 1 | 82 |
| 5 | DEV | 1000 | sc | 4 | 17 | 0 | 0 | 0 | 0 | 0 | 0 | 0 | 0 | 0 | 0 | 0 |

[1]Day of age at inoculation
[2]Number of birds died between 9-day to 19-days of age The above results show that injection of wtDEV at Day 4 post-hatch is safe with 100% survival rate (see group 5). In sharp contrast, after in ovo injection of DEV, 100% of birds died by 4-days of age, while in ovo injection of PBS is safe. These results thus show that, while wtDEV may be suitable for administration to adult animals, surprisingly, it is lethal in young animals (Day 3 or less post hatch) or when administered in ovo.

Example 2: Construction of DEV Comprising an Inactive UL4 Gene

2.1 Construction of rpsLneo-DsRed2 Cassette

A 2.8-kb DNA fragment of rpsLneo-DsRed2 cassette was constructed by PCR reactions. Briefly, three PCR reactions were conducted. First PCR reaction was conducted using primer pair of SEQ ID NO: 1 (5'-GGCCTGGTGATGATG-GCGGGATCGTTGTAT-3') and SEQ ID NO: 2 (5'-CCATG-GTGCTGCGCTCAGAAGAACTCGTCA-3') with the template of synthesized fragment of rpsLneo (SEQ ID NO: 3). Second PCR reaction was conducted using primer pair of SEQ ID NO: 4 (5'-ACGAGTTCTTCTGAGCGCAGCAC-CATGGCC-3') and SEQ ID NO: 5 (5'-TCGGAGGAGGC-CATCCTTAAGAGCTGTAAT-3') with the template plasmid of pSI Mammalian Expression Vectors (Promega, Cat # E1721). Third PCR reaction was conducted using primer pair of SEQ ID NO: 6 (5'-TACAGCTCTTAAGGATGGC-CTCCTCCGAGA-3') and SEQ ID NO: 7 (5'-GCAGT-GAAAAAAATGCTTTATTTGTGAAAT-3') with the template plasmid of pIRES2-DsRed2 (Clontech, Cat #632420). Another PCR reaction was conducted using a mixture of PCR products from the first and second PCR reactions as a template and SEQ ID NO: 1 and SEQ ID NO: 5 as primers. This PCR product and the PCR product from third PCR reaction were mixed and used for final PCR reaction with primer pair of SEQ ID NO:1 and SEQ ID NO:7, resulting in rpsLneo-DsRed2 cassette.

2.2. Construction of Insertion Cassette

A DNA fragment of rpsLneo-DsRed2 cassette that was added Duck enteritis virus (DEV) UL4 region homologous sequences (50 bp each) of both 5' and 3' ends to both ends of it was constructed by PCR reaction (FIG. 1). PCR reaction was conducted using rpsLneo-DsRed2 cassette as a template. Primer pair used is SEQ ID NO: 8 (5'-ATG-CAATCGCATCCGGCAACGTTTATAACTTA-CACTCTGGGGGGTACCGGGGCCT GGTGATGATG-GCGGG-3') and SEQ ID NO: 9 (5'-TTAAATGTCTATACCGTTCACTGCAATTGGCTCCTG-AGACGTTCCATTGCGCAGT GAAAAAAATGCTTTA-3'). Obtained PCR fragment was electrophoresed and purified.

2.3. Construction of Recombinant DEV Carrying rpsLneo-DsRed2 Gene

Construction of recombinant DEV carrying rpsLneo-DsRed2 gene in UL4 region was conducted by homologous recombination in E. coli. strain carrying DEV genome was transfected with 0.1 µg of the insertion cassette. Transfection was conducted by electroporation using Gene Pulser Xcell (Bio-Rad Laboratories) at 1.75 kV, 25 µF, and 200 ohm. After transfection, the E. coli was planted onto Luria-Bertani (LB) agar plates, and incubated overnight at 30° C. E. coli clones carrying an appropriate insert containing the rpsLneo-DsRed2 gene were identified by PCR using primer pair amplifying a region between rpsLneo-DsRed2 gene and the insertion site region of DEV genome (Junction 1, FIG. 2). The primers are SEQ ID NO: 10 (5'-TGTTTAGCGT-TATCCGCCCACTGTGTAAAC-3') and SEQ ID NO: 11 (5'-TCAGAAGAACTCGTCAAGAAGGC-3'). Modified DEV DNA was extracted from E. coli clones carrying an appropriate insert and transfected into CEF cells using Nucleofector II (Lonza, Basel, Switzerland). The transfected cells were added to Leibovitz's L-15 (Life Technologies Corp., Cat. #41300-39), McCoy's 5A Medium (Life Technologies Corp., Cat. #21500-061) (1:1) and 4% calf serum [LM (+) medium], planted in 96-well tissue culture plates, and then incubated at 37° C. in 4-5% $CO_2$ for 5-7 days until DEV cytopathic effect (CPE) became visible.

2.4. Verification of Genome Structure

Figure 2:
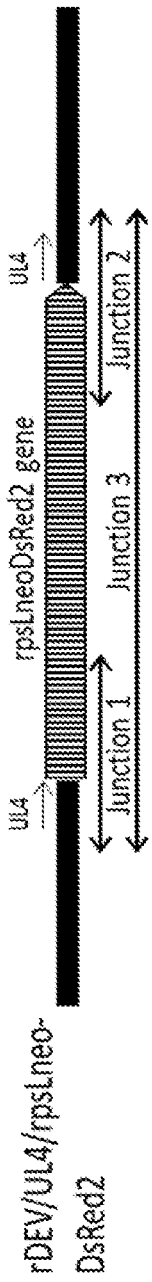
Figure 3:
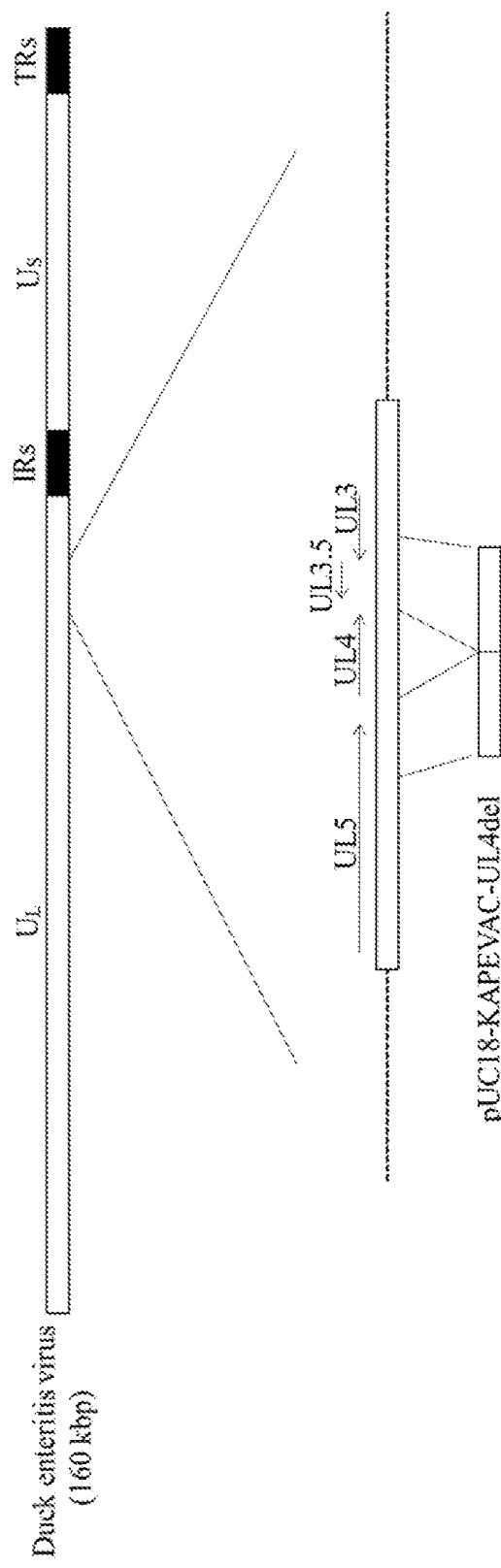

Genome structure of the recombinant DEV/UL4/rpsLneo-DsRed2 was verified by three PCR reactions amplifying junction regions (Junction 1, Junction 2, and Junction 3; FIG. 2) at each end of the inserted gene. The primer pairs used in the PCR reactions for Junction 1 are described in Example 2.3. The primer pair used in the PCR reactions for Junction 2 is SEQ ID NO: 6 and SEQ ID NO: 12 (5'-GGGAGTATTCACAAAATAATAAACAAAC-3'). For Junction 3, SEQ ID NO: 10 and SEQ ID NO: 12 are used.

Expected sizes of PCR products were observed, confirming that rDEV/UL4/rpsLneo-DsRed2 had the expected genome structure.

Figure 4:
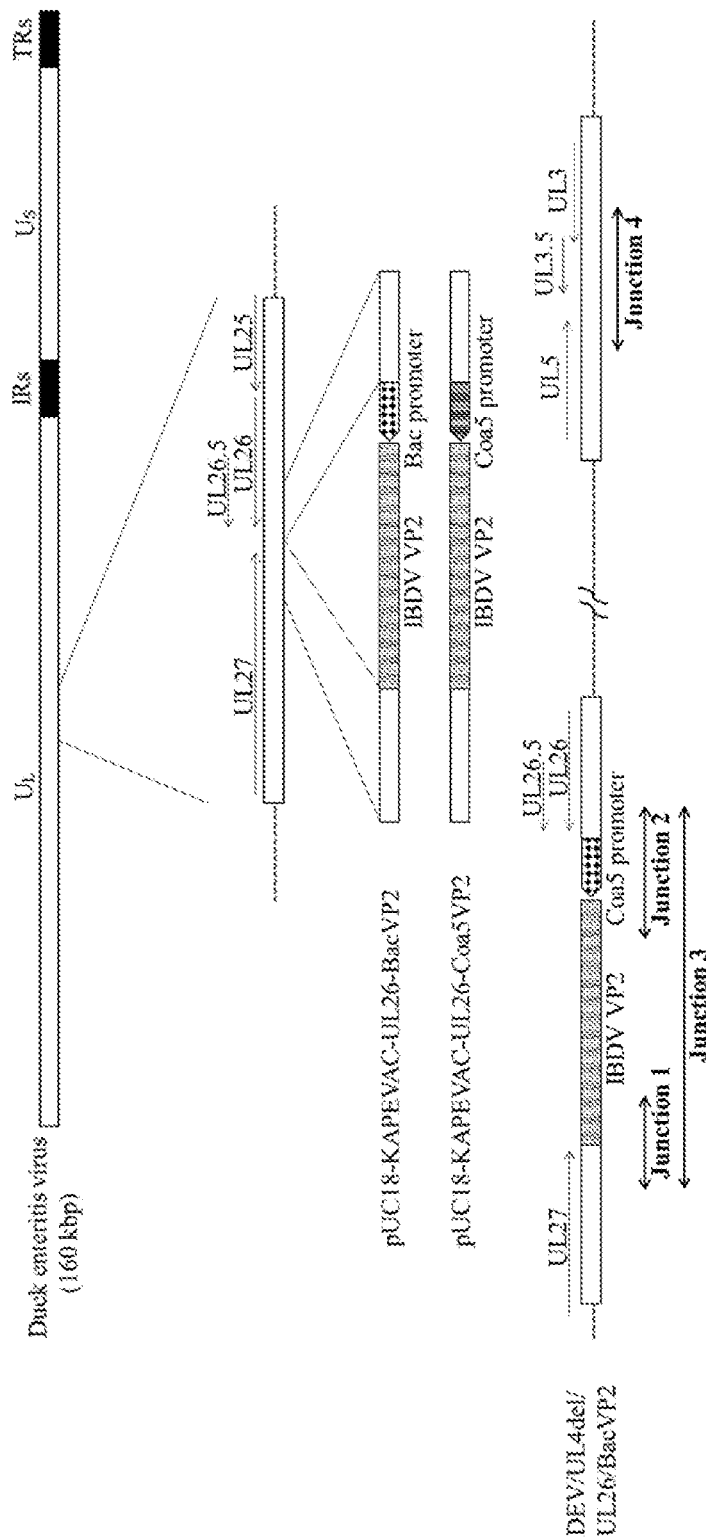
Figure 5:
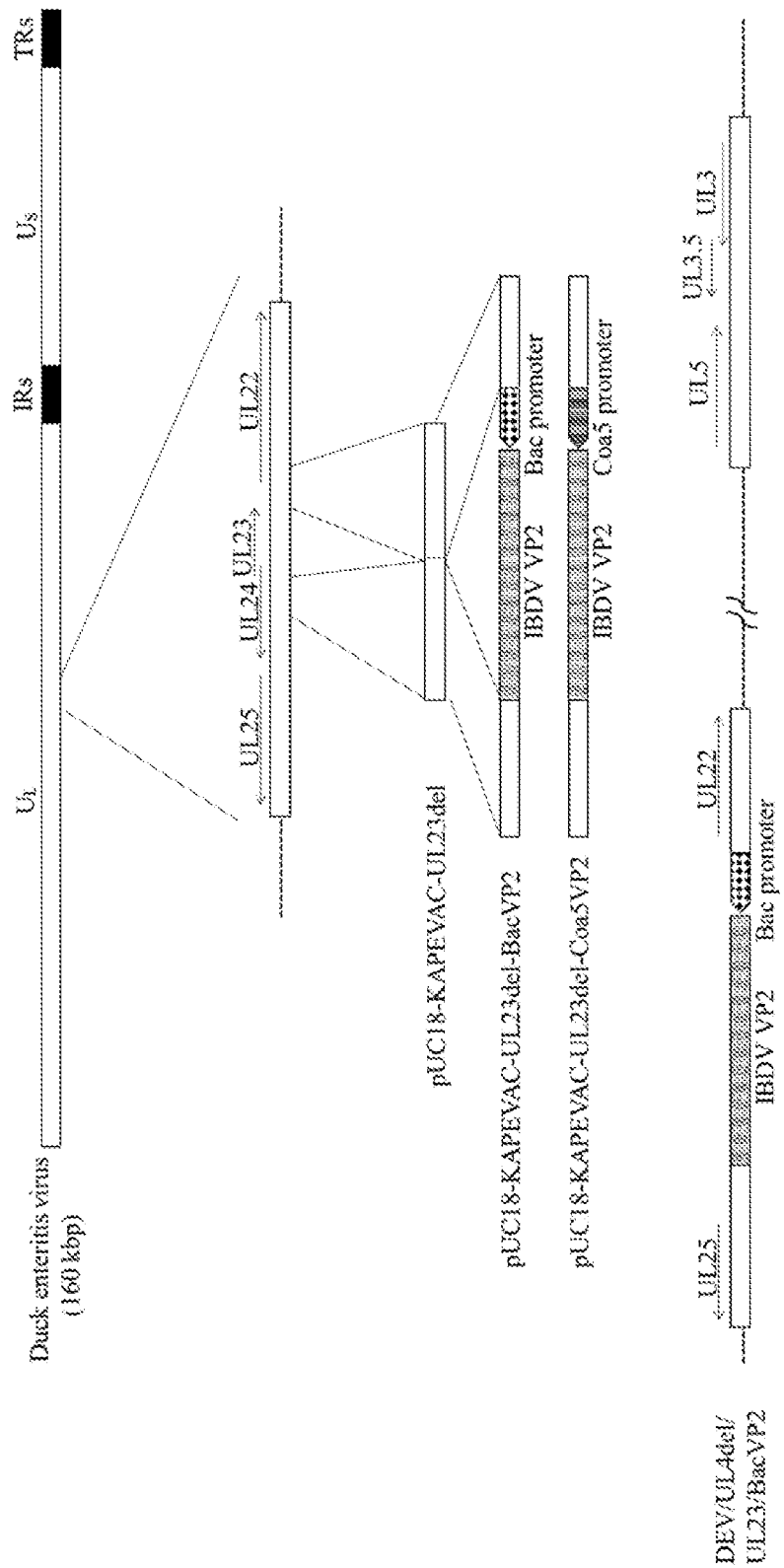
Figure 6:
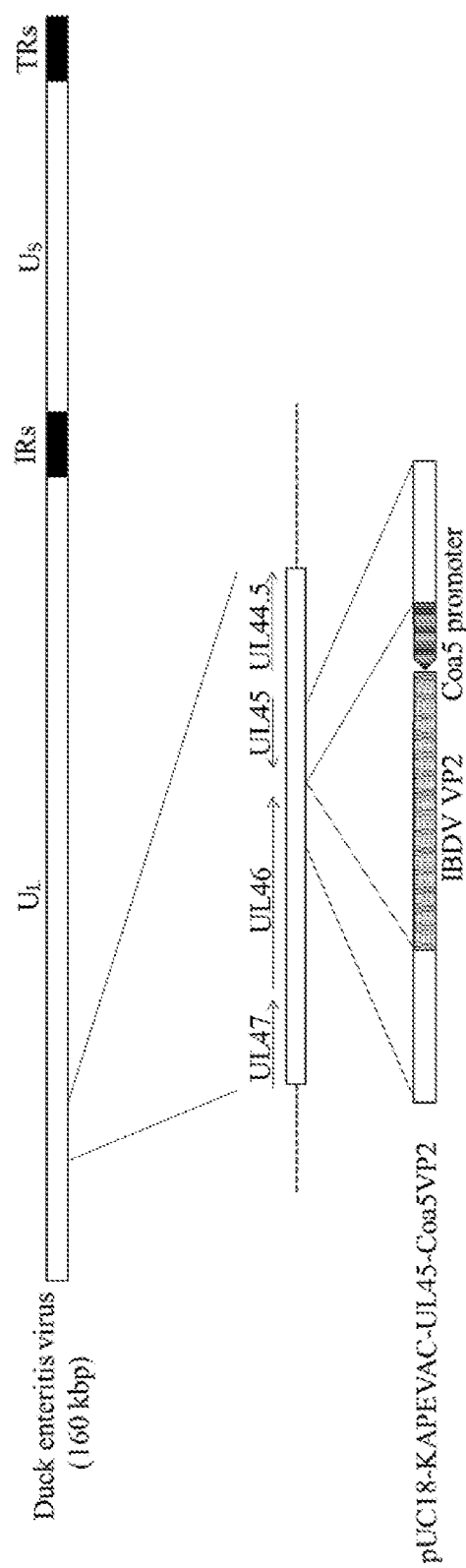
Figure 8:
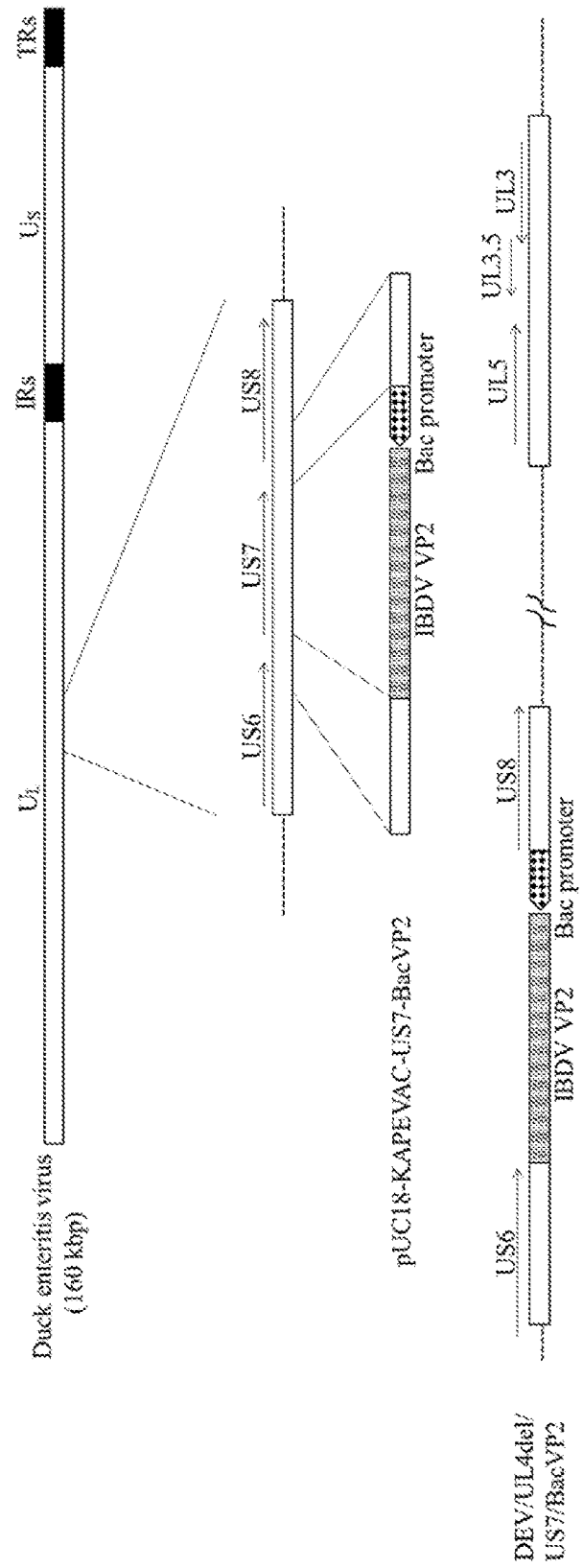

Example 3: Expression of Foreign Gene by Recombinant DEV Having Inactive UL4 Gene Expression of the DsRed2 protein by the recombinant DEV/UL4/rpsLneo-DsRed2 was confirmed by excitation for DsRed2. Excitation for DsRed2 was conducted using CEF cells infected with the recombinant DEV/UL4/rpsLneo-DsRed2. Briefly, CEF cells in 6-well plate were infected with the rDEV/UL4/rpsLneo-DsRed2 or the parent DEV strain at a multiplicity of infection of approximately 0.01. Three days post inoculation, cells were excited at 563 nm. Red fluorescence was only observed in the plaques of recombinant DEV/UL4/rpsLneo-DsRed2.

Example 4: Viability and Stability of Recombinant DEV Having Inactive UL4 Gene

Recombinant DEV/UL4/rpsLneo-DsRed2 was passaged in CEF cells at fifteen times and confirmed stability of inserted gene of rpsLneo-DsRed2. Passage was conducted every three to four days. Every five passages, plaques of rDEV/UL4/rpsLneo-DsRed2 were checked red fluorescence by fluorescence microscope and genome structure of rDEV/UL4/rpsLneo-DsRed2 was confirmed by PCR analysis amplifying junction regions (Junction 1, Junction 2, and Junction 3; FIG. 2) with the primers shown in Example 2.4. Red fluorescence and expected sizes of PCR products were observed all of the observed viruses, confirming that rDEV/UL4/rpsLneo-DsRed2 retained rpsLneo-DsRed2 gene for at least fifteen passages.

Example 5: In Ovo Administration

Recombinant DEV/UL4/rpsLneo-DsRed2 or parental DEV was inoculated into 18-days-old embryo of specific pathogen free (SPF) chickens or commercial layer (white leghorn) chickens with maternal antibodies. All groups of embryos are vaccinated in ovo with approximately 1000 pfu/0.1 ml of the recombinant DEV/UL4/rpsLneo-DsRed2, parental DEV or PBS via 20 gauge and 1.5 inch needles. The hatched chicks are bled each week between 1 and 3 weeks of age. Chicks are observed daily for clinical signs associated with DEV, such as depression and death. Three weeks post hatch, chicks are examined for weight gain and necropsied and observed for grossly observable lesions.

| | | | Number of birds to death in each day of age | | | | | | | | | |
|---|---|---|---|---|---|---|---|---|---|---|---|---|
| Vaccine | n | Not hatch | D0 | D1 | D2 | D3 | D4 | D5 | >D6-D8[1] | D9 | D10-D11[2] | % Mortality |
| PBS | 22 | 2 | 0 | 0 | 0 | 0 | 2 | 0 | 0 | 0 | 0 | 18 |
| DEV/UL4/rpsLneo-DsRed2 | 22 | 0 | 0 | 0 | 0 | 0 | 5 | 2 | 0 | 1 | 0 | 36 |
| DEV | 22 | 0 | 6 | 1 | 8 | 4 | 2 | 0 | 0 | 0 | 0 | 95 |

[1]Number of birds died between 6-day to 8-days of age

[2]Number of birds died between 10-day to 11-days of age

The results are shown above. While almost all birds inoculated with parental DEV died, more than 60% birds inoculated with DEV/UL4/rpsLneo-DsRed2 survived.

Example 6: Construction and In Ovo Administration of a DEV Having an Inactive UL4 Gene and a Foreign Gene Sequence Inserted Between UL27 and UL26

DEV having an inactive UL4 gene and a foreign gene sequence inserted between UL27 and UL26 was constructed.

6.1. Construction of pUC18-KAPEVAC-UL4del

A 1.0-kb DNA fragment of DEV genome flanking the UL5 and UL3.5 genes was cloned by PCR reactions adding SfiI recognition site at the insertion site (FIG. 3). Briefly, using DNA extracted from DEV as a template, two PCR reactions were conducted. Primer pairs used are SEQ ID NO: 14 (5'-gcGCATGCACTATAGCGCGCTCACAG-3') and SEQ ID NO: 15 (5'-CAGACCTAAAGGTTAGGCCGTCTGTGAATG-3'), and SEQ ID NO: 16 (5'-CATTCACAGACGGCCTAACCTTTAGGTCTG-3') and SEQ ID NO: 17 (5'-gcGAATTCCGCAAACTACACAAGTCCG-3'). Another PCR reaction was conducted using a mixture of PCR products from the two previous PCR reactions as a template and SEQ ID NO: 14 and SEQ ID NO: 17 as primers. An obtained PCR fragment was cloned into pUC18 vector after digestion with SphI and EcoRI, resulting in pUC18-KAPEVAC-UL4del (FIG. 3).

6.2. Construction of pUC18-KAPEVAC-UL26-BacVP2

A 1.0-kb DNA fragment of DEV genome flanking the UL26 and UL27 genes was cloned by PCR reactions adding SfiI recognition site at the insertion site (FIG. 4). Briefly, using DNA extracted from DEV as a template, two PCR reactions were conducted. Primer pairs used are SEQ ID NO: 18 (5'-CGGTCGACACTCCCAGGGGTGAAGC-3') and SEQ ID NO: 19 (5'-CGGCCAATAAGGCCAAGAATGCATTCGGCC-3'), and SEQ ID NO: 20 (5'-TGGCCTTATTGGCCGCCGTATGAATTGCGC-3') and SEQ ID NO: 21 (5'-GCGAGCTCCTGCAACCACAGACCGC-3'). Another PCR reaction was conducted using a mixture of PCR products from the two previous PCR reactions as a template and SEQ ID NO: 18 and SEQ ID NO: 21 as primers. An obtained PCR fragment was cloned into pUC18 vector after digestion with SalI and SacI, resulting in pUC18-KAPEVAC-UL26-SfiI. Next, a homology vector containing a promoter and IBDV VP2 gene from standard challenge strain was constructed by utilizing plasmid pUC18-KAPEVAC-UL26-SfiI. First, pUC18-KAPEVAC-UL26-SfiI was cleaved with SfiI and dephosphorylated with PAP. The Bac promoter-VP2-STC cassette was obtained by BglI digestion of p45/46bacVP2-STC #11 (U.S. Pat. No.

6,764,684) and inserted into the SfiI-digested pUC18-KAPEVAC-UL26-SfiI, resulting in pUC18-KAPEVAC-UL26-BacVP2 (FIG. 4). This plasmid was used to construct DEV/UL4del/UL26/BacVP2.

6.3. Construction of DEV Having an Inactive UL4 Gene and a Foreign Gene Sequence Inserted Between UL27 and UL26

Construction of recombinant DEV having an inactive UL4 gene and a foreign gene sequence inserted between UL27 and UL26 region was conducted by homologous recombination in an *E. coli* strain carrying DEV genome and transfected with 0.1 μg of the pUC18-KAPEVAC-UL4del and pUC18-KAPEVAC-UL26-BacVP2. Transfection was conducted by electroporation using Gene Pulser Xcell (Bio-Rad Laboratories) at 1.75 kV, 25 g, and 200 ohm. After transfection, the *E. coli* was planted onto Luria-Bertani (LB) agar plates, and incubated overnight at 30° C. *E. coli* clones carrying an appropriate insert containing the rpsLneo-DsRed2 gene were identified by PCR using primer pair amplifying a region between UL3.5 and UL5 genes (Junction 4; FIG. 4) or a region between Bac-VP2 genes and the insertion site region of DEV genome (Junction 1, FIG. 4). The primers are SEQ ID NO: 14 and SEQ ID NO:17 for Junction 4, and SEQ ID NO: 22 (5'-GACGCTATACCCAATGACGATGAAAAC-3') and SEQ ID NO: 23 (5'-GAGCAACTTCGAGCTGATCC-3') for Junction 1. Modified DEV DNA was extracted from *E. coli* clones carrying an appropriate insert and transfected into CEF cells using Nucleofector II. The transfected cells were added to LM (+) medium, planted in 96-well tissue culture plates, and then incubated at 37° C. in 4-5% $CO_2$ for 5-7 days until DEV CPE became visible.

6.4. Verification of Genome Structure

Genome structure of the recombinant DEV/UL4del/UL26/BacVP2 was verified by four PCR reactions amplifying junction regions (Junction 1, Junction 2, and Junction 3; FIG. 4) at each end of the inserted gene. The primer pairs used in the PCR reactions for Junction 1 and Junction 4 are described in Example 6.3. The primer pair used in the PCR reactions for Junction 2 is SEQ ID NO: 24 (5'-GTACTGCCCGGCCGGTCTAATG-3') and SEQ ID NO: 25 (5'-GCCAGGGAATCCAGGGAAAAAGAC-3'). For Junction 3, SEQ ID NO: 22 and SEQ ID NO: 24 are used. Expected sizes of PCR products were observed, confirming that rDEV/UL4del/BacVP2 had the expected genome structure.

6.5. In Ovo Administration 18-days-old chick embryos were administered 1000 plaque forming unit of rDEV/UL4del/UL26/BacVP2 or parental KAPEVAC virus in ovo at DOA 3. Clinical signs of the birds were observed for 35 days after hatch. The results of 17 birds show a survival rate above 80%.

Example 7: Construction and In Ovo Administration of DEVs Having an Inactive UL4 Gene and an Inactive UL23 Gene DEVs having an inactive UL4 and UL23 gene and a foreign gene were constructed.

7.1. Construction of pUC18-KAPEVAC-UL23-BacVP2 and pUC18-KAPEVAC-UL23-Coa5VP2

A 1.0-kb DNA fragment of DEV genome flanking the UL24 and UL22 genes was cloned by PCR reactions adding SfiI recognition site at the insertion site (FIG. 5). Briefly, using DNA extracted from DEV as a template, two PCR reactions were conducted. Primer pairs used are SEQ ID NO: 26 (5'-GCGCATGCCAATTGTCTAATTCCAG-3') and SEQ NO: 27 (5'-CCCGGCCAATAAGGCCACAGAAAAAGCGCG-3'), and SEQ ID NO: 28 (5'-CTGTGGCCTTATTGGCCGGGATCTGGAAC-3') and SEQ ID NO: 29 (5'-GCGAATTCATGTGCTACGCCCAG-3'). Another PCR reaction was conducted using a mixture of PCR products from the two previous PCR reactions as a template and SEQ ID NO: 26 and SEQ ID NO: 29 as primers. An obtained PCR fragment was cloned into pUC18 vector after digestion with EcoRI and SphI, resulting in pUC18-KAPEVAC-UL23del-SfiI. Next, a homology vector containing a promoter and VP2-STC was constructed by utilizing plasmid pUC18-KAPEVAC-UL23 del-SfiI. First, pUC18-KAPEVAC-UL23 del-SfiI was cleaved with SfiI and dephosphorylated with PAP. The Bac-VP2 cassette was obtained from the plasmid pUC18-KAPEVAC-UL26-BacVP2 by SfiI digestion and inserted into SfiI-digested ligated pUC18-KAPEVAC-UL23del-SfiI, resulting in pUC18-KAPEVAC-UL23-BacVP2 (FIG. 5). In addition, pUC18-KAPEVAC-UL23-Coa5VP2 was constructed by utilizing pUC18-KAPEVAC-UL23-SfiI. The Coa5 promoter was obtained from the plasmid pGICOA (U.S. Pat. No. 6,866,852) by BglI and XbaI digestion, and ligated with a XbaI-EcoRI fragment (6.3-kb) and an EcoRI-BglI fragment (0.1-kb) of p45/46bacVP2-STC #11 (U.S. Pat. No. 6,764,684), resulting in p45/46COA5VP2-STC #11. The Coa5 promoter-VP2-STC cassette was then cut out from p45/46COA5VP2-STC #11 by BglI digestion and ligated with the SfiI-digested pUC18-KAPEVAC-UL23 del-SfiI, resulting in pUC18-KAPEVAC-UL23del-Coa5VP2 (FIG. 5).

7.2. Construction of pUC18-KAPEVAC-UL26-Coa5VP2 pUC18-KAPEVAC-UL26-Coa5VP2 was constructed by utilizing the SfiI-digested pUC18-KAPEVAC-UL26-SfiI. Coa5-VP2 cassette was obtained from pUC18-KAPEVAC-UL23-Coa5VP2 by SfiI digestion and inserted into SfiI-digested pUC18-KAPEVAC-UL26-SfiI, resulting in pUC18-KAPEVAC-UL26-Coa5VP2 (FIG. 4).

7.3. Construction of pUC18-KAPEVAC-UL45-Coa5VP2

A 1.0-kb DNA fragment of DEV genome flanking the UL45 and UL46 genes was cloned by PCR reactions adding SfiI recognition site at the insertion site (FIG. 6). Briefly, using DNA extracted from DEV as a template, two PCR reactions were conducted. Primer pairs used are SEQ ID NO: 30 (5'-CGGTCGACATAGAACGCGCTTCATCTAA-3') and SEQ ID NO: 31 (5'-TGGCCAATAAGGCCGTTTATTGTTTATTAT-3'), and SEQ ID NO: 32 (5'-CGGCCTTATTGGCCAATCTGATTCATCCAA-3') and SEQ ID NO: 33 (5'-GCGAGCTCCGCCTAATCACAATCGGTATTG-3'). Another PCR reaction was conducted using a mixture of PCR products from the two previous PCR reactions as a template and SEQ ID NO: 30 and SEQ ID NO: 33 as primers. An obtained PCR fragment was cloned into pUC18 vector after digestion with SalI and SacI, resulting in pUC18-KAPEVAC-UL45-SfiI. Next, a homology vector containing a promoter and IBDV VP2 gene from standard challenge strain was constructed by utilizing plasmid pUC18-KAPEVAC-UL45-SfiI. First, pUC18-KAPEVAC-UL45-SfiI was cleaved with SfiI and dephosphorylated with PAP. The Coa5 promoter-VP2-STC cassette was cut out from pUC18-KAPEVAC-UL23del-Coa5VP2 by SfiI digestion and ligated with the SfiI-digested pUC18-KAPEVAC-UL45-SfiI, resulting in pUC18-KAPEVAC-UL45-Coa5VP2 (FIG. 6).

7.4. Construction of pUC18-KAPEVAC-UL50-Coa5VP2

A 1.0-kb DNA fragment of DEV genome flanking the UL50 and UL51 genes was cloned by PCR reactions adding SfiI recognition site at the insertion site (FIG. 7). Briefly, using DNA extracted from DEV as a template, two PCR reactions were conducted. Primer pairs used are SEQ ID NO: 34 (5'-CCGCATGCGCAACTATATATGTCGGTC-3') and SEQ ID NO: 35 (5'-GGGCCAATAAGGCCCAAAAG-TACATTTTGT-3'), and SEQ ID NO: 36 (5'-GGGCCTTAT-TGGCCCAATTTATTTACTATT-3') and SEQ ID NO: 37 (5'-GCGAATTCTGGATATGATATACCGTTGC-3'). Another PCR reaction was conducted using a mixture of PCR products from the two previous PCR reactions as a template and SEQ ID NO: 34 and SEQ ID NO: 37 as primers. An obtained PCR fragment was cloned into pUC18 vector after digestion with EcoRI and SphI, resulting in pUC18-KAPEVAC-UL50-SfiI. Next, a homology vector containing a promoter and IBDV VP2 gene from standard challenge strain was constructed by utilizing plasmid pUC18-KAPEVAC-UL50-SfiI. First, pUC18-KAPEVAC-UL50-SfiI was cleaved with SfiI and dephosphorylated with PAP. The Coa5 promoter-VP2-STC cassette was cut out from pUC18-KAPEVAC-UL23del-Coa5VP2 by SfiI digestion and ligated with the SfiI-digested pUC18-KAPEVAC-UL50-SfiI, resulting in pUC18-KAPEVAC-UL50-Coa5VP2. This plasmid was used to construct DEV/US4US5del/UL50/Coa5VP2 (FIG. 7).

7.5. Construction of pUC18-KAPEVAC-UL23del

A 1.0-kb DNA fragment of DEV genome flanking the UL24 and UL22 genes was cloned by PCR reactions adding SfiI recognition site at the insertion site (FIG. 5). Briefly, using DNA extracted from DEV as a template, two PCR reactions were conducted. Primer pairs used are SEQ ID NO: 26 and SEQ ID NO: 38 (5'-CTTGTTCCAGATC-CCACAGAAAAAGCGCG-3'), and SEQ ID NO: 39 (5'-CGCGCTTTTTCTGTGGGATCTGGAACAAG-3') and SEQ ID NO: 29. Another PCR reaction was conducted using a mixture of PCR products from the two previous PCR reactions as a template and SEQ ID NO: 26 and SEQ ID NO: 29 as primers. An obtained PCR fragment was cloned into pUC18 vector after digestion with EcoRI and SphI, resulting in pUC18-KAPEVAC-UL23del (FIG. 5).

7.6. Construction of DEV Having an Inactive UL4 and UL23 Genes and a Foreign Gene Sequence The construction of recombinant DEVs having inactive UL4 and UL23 genes and a foreign gene sequence was conducted by homologous recombination in an *E. coli.* strain carrying DEV genome and transfected with 0.1 μg of the pUC18-KAPEVAC-UL4del and pUC18-KAPEVAC-UL23-BacVP2 for JK015, of the pUC18-KAPEVAC-UL4del, pUC18-KAPEVAC-UL23del, and pUC18-KAPEVAC-UL26-Coa5VP2 for JK022, of the pUC18-KAPEVAC-UL4del, pUC18-KAPEVAC-UL23del, and pUC18-KAPE-VAC-UL45-Coa5VP2 for JK023, or of the pUC18-KAPEVAC-UL4del, pUC18-KAPEVAC-UL23del, and pUC18-KAPEVAC-UL50-Coa5VP2 for JK024. Transfection was conducted as described above and DEVs having an inactive UL4 and UL23 genes and a foreign gene sequence were rescued (JK022-JK024).

| Number | Name | deletion site | insertion site | promoter/ insertion gene/polyA |
|---|---|---|---|---|
| JK015 | rDEV/UL4del/ UL23/BacVP2 | | UL23 | Ba/VP2stc/ SV40polyA |
| JK022 | rDEV/UL4del/ UL23del/UL26/ BacVP2 | UL4, UL23 | UL26/27 | Coa5/VP2stc/ SV40polyA |
| JK023 | rDEV/UL4del/ UL23del/UL45/ Coa5VP2 | UL4, UL23 | UL45/46 | Coa5/VP2stc/ SV40polyA |
| JK024 | rDEV/UL4del/ UL23del/UL51/ Coa5VP2 | UL4, UL23 | UL50/51 | Coa5/VP2stc/ SV40polyA |
| JK025 | rDEV/UL4del/ US7del/UL23/ Coa5VP2 | UL4, UL23, US7 | UL23 | Coa5/VP2stc/ SV40polyA |

JK015, JK022, JK023, and JK024 were successfully rescued.

7.7. Growth Rate

The growth rate of these DEVs was assessed and the results are provided below:

| DEV | Deletion site | Insertion site | Stock titer |
|---|---|---|---|
| JK022 | UL4, UL23 | UL26/27 | 9.6 × 10E4 |
| JK023 | UL4, UL23 | UL45/46 | 8.5 × 10E4 |
| JK024 | UL4, UL23 | UL50/51 | 6.1 × 10E4 |
| JK025 | UL4, UL23, US7 | UL23 | 1.57 × 10E4 |

7.8. In Ovo Administration 18-days-old chick embryos were administered 1000 plaque forming unit of the following DEVs or parental KAPEVAC virus in ovo at DOA 3. Clinical signs of the birds were observed for 35 days after hatch. The results are shown in the table below:

| DEV | Deletion site | Insertion site | Number of eggs | Not hatch | Dead birds at day 35 | Survival rate |
|---|---|---|---|---|---|---|
| Non immunized control | — | — | 16 | 0 | 0 | 100% |
| JK015 | UL4, UL23 | UL23 | 17 | 1 | 1 | 94% |
| parental DEV | — | — | 17 | 7 | 10 | 0% |

In this trial, most chickens inoculated with rDEV/UL4del/UL23/BacVP2 survived for the observation period, while all chickens inoculated with parental DEV strain died.

Example 8: Construction and In Ovo Administration of DEVs Having an Inactive UL4 Gene and an Inactive US7 Gene DEVs having an inactive UL4 and US7 genes and a foreign gene were constructed.

8.1. Construction of pUC18-KAPEVAC-US7-BacVP2

A 0.6-kb DNA fragment of DEV genome flanking the US6 and US8 genes was cloned by PCR reactions adding SfiI recognition site at the insertion site (FIG. 8). Briefly, using DNA extracted from DEV as a template, two PCR reactions were conducted. Primer pairs used are SEQ ID NO: 40 (5'-gcGCATGCCCACCCATAGCCTATTAC-3') and SEQ NO: 41 (5'TATGATTGACTGTTTGCCTTTCATTAACATCCAAATATATTTGTACATGAGGTAAT AGGCTATGGGTGCCTTATTGGCCA-3'), and SEQ ID NO: 42 (5'-AACAGTCAATCATAACAAAAACATTTACTTTTAGTCATACTGATGTGAATTAggccttat tggccTTCTATTTTTGAAAC-3') and SEQ ID NO: 43 (5'-gcGAATTCATGACCATGGACATGC-3'). Another PCR reaction was conducted using a mixture of PCR products from the two previous PCR reactions as a template and SEQ ID NO: 40 and SEQ ID NO: 43 as primers. An obtained PCR fragment was cloned into pUC18 vector after digestion with EcoRI and SphI, resulting in pUC18-KAPEVAC-US7del-SfiI. Next, a homology vector containing a promoter and VP2-STC was constructed by utilizing plasmid pUC18-KAPEVAC-US7del-SfiI. First, pUC18-KAPEVAC-US7del-SfiI was cleaved with SfiI and dephosphorylated with PAP. The Bac-VP2 cassette was obtained from the plasmid pUC18-KAPEVAC-UL26-BacVP2 by SfiI digestion and inserted into SfiI-digested ligated pUC18-KAPEVAC-US7del-SfiI, resulting in pUC18-KAPEVAC-US7-BacVP2 (FIG. 8).

8.2. Construction of pUC18-KAPEVAC-US7del

A 0.6-kb DNA fragment of DEV genome flanking the US6 and US8 genes was cloned by PCR reactions (FIG. 8). Briefly, using DNA extracted from DEV as a template, two PCR reactions were conducted. Primer pairs used are SEQ ID NO: 40 and SEQ NO: 44 (5'-GTGCGCCATATAGACGTAATTCACATCAG-3'), and SEQ ID NO: 45 (5'-CTGATGTGAATTACGTCTATATGGCGCAC-3') and SEQ ID NO: 43. Another PCR reaction was conducted using a mixture of PCR products from the two previous PCR reactions as a template and SEQ ID NO: 40 and SEQ ID NO: 43 as primers. An obtained PCR fragment was cloned into pUC18 vector after digestion with EcoRI and SphI, resulting in pUC18-KAPEVAC-US7del (FIG. 8).

8.3. Construction of DEV Having an Inactive UL4 and US7 Genes and a Foreign Gene Sequence Construction of recombinant DEVs having inactive UL4 and US7 genes and a foreign gene sequence was conducted by homologous recombination in an *E. coli* strain carrying DEV genome and transfected with 0.1 μg of the pUC18-KAPEVAC-UL4del and pUC18-KAPEVAC-US7-BacVP2 for JK016, of the pUC18-KAPEVAC-UL4del, pUC18-KAPEVAC-US7del, and pUC18-KAPEVAC-UL23del-Coa5VP2 for JK025, of the pUC18-KAPEVAC-UL4del, pUC18-KAPEVAC-US7del, and pUC18-KAPEVAC-UL26-Coa5VP2 for JK026, of the pUC18-KAPEVAC-UL4del, pUC18-KAPEVAC-US7del, and pUC18-KAPEVAC-UL45-Coa5VP2 for JK027, or of the pUC18-KAPEVAC-UL4del, pUC18-KAPEVAC-US7del, and pUC18-KAPEVAC-UL50-Coa5VP2 for JK028. Transfection was conducted as described above and DEVs having an inactive UL4 and US7 genes and a foreign gene sequence were rescued (JK016, and JK025-JK028).

| Number | Name | deletion site | insertion site | promoter/ insertion gene/polyA |
|---|---|---|---|---|
| JK016 | rDEV/UL4del/ US7/BacVP2 | UL4, US7 | US7 | Bac/VP2stc/ SV40polyA |
| JK025 | rDEV/UL4del/ US7del/UL23/ Coa5VP2 | UL4, UL23, US7 | UL23 | Coa5/VP2stc/ SV40polyA |
| JK026 | rDEV/UL4del/ US7del/UL26/ Coa5VP2 | UL4, US7 | UL26/27 | Coa5/VP2stc/ SV40polyA |
| JK027 | rDEV/UL4del/ US7del/UL45/ Coa5VP2 | UL4, US7 | UL45/46 | Coa5/VP2stc/ SV40polyA |
| JK028 | rDEV/UL4del/ US7del/UL50/ Coa5VP2 | UL4, US7 | UL50/51 | Coa5/VP2stc/ SV40polyA |

JK016, JK025-JK028 were successfully constructed.

8.4. Growth Rate

The growth rate of these DEVs was assessed and the results are provided below:

| DEV | Deletion site | Insertion site | Stock titer |
|---|---|---|---|
| JK025 | UL4, UL23, US7 | UL23 | 1.57 × 10E4 |
| JK026 | UL4, US7 | UL26/27 | 5.2 × 10E4 |
| JK027 | UL4, US7 | UL45/46 | 1.18 × 10E5 |
| JK028 | UL4, US7 | UL50/51 | 2.2 × 10E5 |

8.5. In Ovo Administration 18-days-old chick embryos were administered 1000 plaque forming unit of the following DEVs or parental KAPEVAC virus in ovo at DOA 3. Clinical signs of the birds were observed for 35 days after hatch. The results are shown in the table below:

| DEV | Deletion site | Insertion site | Number of eggs | Not hatch | Dead birds at day 35 | Survival rate |
|---|---|---|---|---|---|---|
| Non immunized control | — | — | 16 | 0 | 0 | 100% |
| JK016 | UL4, US7 | US7 | 17 | 0 | 0 | 100% |
| Parental DEV | — | — | 17 | 7 | 10 | 0% |

In this trial, all the chickens inoculated with rDEV/UL4del/US7/BacVP2 survived for 35 days.

LIST OF SEQUENCES

SEQ ID NO: 1 F-rpsL: (5'- GGCCTGGTGATGATGGCGGGATCGTTGTAT -3')

SEQ ID NO: 2 R-SV40promoter-neoR-rpsL: (5'- CCATGGTGCTGCGCTCAGAAGAACTCGTCA -3')

SEQ ID NO: 3 rpsLneo: (5'-
GGCCTGGTGATGATGGCGGGATCGTTGTATATTTCTTGACACCTTTTCGGCATCGCCCTAAAATTC
GGCGTCCTCATATTGTGTGAGGACGTTTTATTACGTGTTTACGAAGCAAAAGCTAAAACCAGGAGC
TATTTAATGGCAACAGTTAACCAGCTGGTACGCAAACCACGTGCTCGCAAAGTTGCGAAAAGCAA
CGTGCCTGCGCTGGAAGCATGCCCGCAAAAACGTGGCGTATGTACTCGTGTATATACTACCACTCC
TAAAAAACCGAACTCCGCGCTGCGTAAAGTATGCCGTGTTCGTCTGACTAACGGTTTCGAAGTGAC
TTCCTACATCGGTGGTGAAGGTCACAACCTGCAGGAGCACTCCGTGATCCTGATCCGTGGCGGTCG
TGTTAAAGACCTCCCGGGTGTTCGTTACCACACCGTACGTGGTGCGCTTGACTGCTCCGGCGTTAA
AGACCGTAAGCAGGCTCGTTCCAAGTATGGCGTGAAGCGTCCTAAGGCTTAAGGAGGACAATCAT
GATTGAACAAGATGGATTGCACGCAGGTTCTCCGGCCGCTTGGGTGGAGAGGCTATTCGGCTATG
ACTGGGCACAACAGACAATCGGCTGCTCTGATGCCGCCGTGTTCCGGCTGTCAGCGCAGGGGCGC
CCGGTTCTTTTTGTCAAGACCGACCTGTCCGGTGCCCTGAATGAACTGCAGGACGAGGCAGCGCGG
CTATCGTGGCTGGCCACGACGGGCGTTCCTTGCGCAGCTGTGCTCGACGTTGTCACTGAAGCGGGA
AGGGACTGGCTGCTATTGGGCGAAGTGCCGGGGCAGGATCTCCTGTCATCTCACCTTGCTCCTGCC
GAGAAAGTATCCATCATGGCTGATGCAATGCGGCGGCTGCATACGCTTGATCCGGCTACCTGCCCA
TTCGACCACCAAGCGAAACATCGCATCGAGCGAGCACGTACTCGGATGGAAGCCGGTCTTGTCGA
TCAGGATGATCTGGACGAAGAGCATCAGGGGCTCGCGCCAGCCGAACTGTTCGCCAGGCTCAAGG
CGCGCATGCCCGACGGCGAGGATCTCGTCGTGACCCATGGCGATGCCTGCTTGCCGAATATCATGG
TGGAAAATGGCCGCTTTTCTGGATTCATCGACTGTGGCCGGCTGGGTGTGGCGGACCGCTATCAGG
ACATAGCGTTGGCTACCCGTGATATTGCTGAAGAGCTTGGCGGCGAATGGGCTGACCGCTTCCTCG
TGCTTTACGGTATCGCCGCTCCCGATTCGCAGCGCATCGCCTTCTATCGCCTTCTTGACGAGTTCTT
CTGA -3')

SEQ ID NO: 4 F-neoR-SV40promoter: (5'- ACGAGTTCTTCTGAGCGCAGCACCATGGCC -3')

SEQ ID NO: 5 R-dsRed-SV40promoter-intron: (5'- TCGGAGGAGGCCATCCTTAAGAGCTGTAAT -3')

SEQ ID NO: 6 F-SV40promoter-intron-dsRed: (5'- TACAGCTCTTAAGGATGGCCTCCTCCGAGA -3')

SEQ ID NO: 7 R-SV40polyA-dsRed: (5'- GCAGTGAAAAAAATGCTTTATTTGTGAAAT -3')

SEQ ID NO: 8 F-DEV-UL4-rpsLneo: (5'-
ATGCAATCGCATCCGGCAACGTTTATAACTTACACTCTGGGGGGTACCGGGGCCTGGTGATGATGG
CGGG -3')

SEQ ID NO: 9 R-DEV-UL4-rpsLneoSV40DsRed: (5'-
TTAAATGTCTATACCGTTCACTGCAATTGGCTCCTGAGACGTTCCATTGCGCAGTGAAAAAAATGC
TTTA -3')

SEQ ID NO: 10 F-VAC-109228: (5'- TGTTTAGCGTTATCCGCCCACTGTGTAAAC -3')

SEQ ID NO: 11 R-neo: (5'- TCAGAAGAACTCGTCAAGAAGGC -3')

SEQ ID NO: 12 R-VAC-110144: (5'- GGGAGTATTCACAAAATAATAAACAAAC -3')

SEQ ID NO: 13 UL4 gene sequence of a DEV Jansen strain: (5' -
ATGCAATCGCATCCGGCAACGTTTATAACTTACACTCTGGGGGGTACCGGTGCTTCGCATACGTGG
ACTGTTCCAGAATATGAACAAGTGATCTGTTCGTGCGATGGAGGATCGAGATCTGTTCTGGTCGGG
AACAAGACACGCTGTGACAAACTCCCTCCGTGTAATGTTATTATTCAACGCGGCCCTCTTGGGACT
CTATTCGTCGTAGATATTGGGTATGCAATATATTCCTATATGCTACGTTGTGATCTAAAAAAACAA
CAGGTCGGTACATTATCAGCCTCACCTGGTTCATTATATGTAGTTCCGTTTACATCATGTACCGTAG
TCGGAGTAGATAGCTACATCCGCAGTGACTCTAGTGGTGTATTAACGATTGCATGGTCTCATAATA
CAGTGCATATAACAATAACTGTATATGGTCTGTCGGAAGAGTCTCAGCGCATGGCAAGCGTTTCGG
CCATATCTACTGTCGGGCAAGACTATGAAAATCTTCAGGATATAGCCAACCAAGAGCAAAGTGAA
GATTTACTATCTGCTGCAATAAAAGAAGCTAATATTGGTGTCGACTACATATCAGATAGTGAGTCG
TCATCTAGAACGGTTATGGACGACTTACTAACTTCTATTCAAGATGAATGCCTAGAGACGGCCGAC
TGCTTCTGCAATGGAACGTCTCAGGAGCCAATTGCAGTGAACGGTATAGACATTTAA -3')

SEQ ID NO: 14 F-SphI-KAPEVAC-111150: (5'- gcGCATGCACTATAGCGCGCTCACAG -3')

SEQ ID NO: 15 R-KAPEUL4del: (5'- CAGACCTAAAGGTTAGGCCGTCTGTGAATG -3')

SEQ ID NO: 16 F-KAPEUL4del: (5'- CATTCACAGACGGCCTAACCTTTAGGTCTG -3')

SEQ ID NO: 17 R-EcoRI-KAPEVAC-112880: (5'- gcGAATTCCGCAAACTACACAAGTCCG -3')

SEQ ID NO: 18 F-SalI-VAC68400: (5'- CGGTCGACACTCCCAGGGGTGAAGC -3')

SEQ ID NO: 19 R-SfiI-UL26-27-insertion: (5'- CGGCCAATAAGGCCAAGAATGCATTCGGCC -3')

SEQ ID NO: 20 F-SfiI-UL26-27-insertion: (5'- TGGCCTTATTGGCCGCCGTATGAATTGCGC -3')

SEQ ID NO: 21 R-SacI-VAC69400: (5'- GCGAGCTCCTGCAACCACAGACCGC -3')

SEQ ID NO: 22 F-VAC-68351: (5'- GACGCTATACCCAATGACGATGAAAAC -3')

LIST OF SEQUENCES

SEQ ID NO: 23 STC1109S: (5'- GAGCAACTTCGAGCTGATCC -3')

SEQ ID NO: 24 R-VAC68971: (5'- GTACTGCCCGGCCGGTCTAATG -3')

SEQ ID NO: 25 STC201AS: (5'- GCCAGGGAATCCAGGGAAAAAGAC -3')

SEQ ID NO: 26 F-SphI-KAPEVAC-76350: (5'- GCGCATGCCAATTGTCTAATTCCAG -3')

SEQ ID NO: 27 R-KAPE-UL23del-SfiIinsertion: (5'- CCCGGCCAATAAGGCCACAGAAAAAGCGCG -3')

SEQ ID NO: 28 F-KAPE-UL23del-SfiIinsertion: (5'- CTGTGGCCTTATTGGCCGGGATCTGGAAC -3')

SEQ ID NO: 29 R-EcoRI-KAPEVAC-78350: (5'- GCGAATTCATGTGCTACGCCCAG -3')

SEQ ID NO: 30 F-SalI-VAC21300: (5'- CGGTCGACATAGAACGCGCTTCATCTAA -3')

SEQ ID NO: 31 R-SfiI-UL45-46-insertion: (5'- TGGCCAATAAGGCCGTTTATTGTTTATTAT -3')

SEQ ID NO: 32 F-SfiI-UL45-46-insertion: (5'- CGGCCTTATTGGCCAATCTGATTCATCCAA -3')

SEQ ID NO: 33 R-SacI-VAC22300: (5'- GCGAGCTCCGCCTAATCACAATCGGTATTG -3')

SEQ ID NO: 34 F-SphI-VAC12000: (5'- CCGCATGCGCAACTATATATGTCGGTC -3')

SEQ ID NO: 35 R-SfiI-UL50-51-insertion: (5'- GGGCCAATAAGGCCCAAAAGTACATTTTGT -3')

SEQ ID NO: 36 F-SfiI-UL50-51-insertion: (5'- GGGCCTTATTGGCCCAATTTATTTACTATT -3')

SEQ ID NO: 37 R-EcoRI-VAC13000: (5'- GCGAATTCTGGATATGATATACCGTTGC -3')

SEQ ID NO: 38 R-KAPE-UL23del: (5'- CTTGTTCCAGATCCCACAGAAAAAGCGCG -3')

SEQ ID NO: 39 F-KAPE-UL23del: (5'- CGCGCTTTTTCTGTGGGATCTGGAACAAG -3')

SEQ ID NO: 40 F-SphI-KAPEVAC-US7del-new: (5'- gcGCATGCCCACCCATAGCCTATTAC -3')

SEQ ID NO: 41 R-KAPEUS7del-SfiIinsertion: (5'- TATGATTGACTGTTTGCCTTTCATTAACATCCAAATATATTTGTACATGAGGTAATAGGCTATGGGTGCCTTATTGGCCA -3')

SEQ ID NO: 42 F-KAPEUS7del-SfiIinsertion: (5'- AACAGTCAATCATAACAAAAACATTTACTTTTAGTCATACTGATGTGAATTAggccttattggccTTCTATTTTTGAAAC -3')

SEQ ID NO: 43 R-EcoRI-KAPEVAC-138100: (5'- gcGAATTCATGACCATGGACATGC -3')

SEQ ID NO: 44 R-KAPE-U57del: (5'- GTGCGCCATATAGACGTAATTCACATCAG -3')

SEQ ID NO: 45 F-KAPE-U57del: (5'- CTGATGTGAATTACGTCTATATGGCGCAC -3')

We claim:

1. A Duck Enteritis Virus (DEV) comprising a foreign nucleic acid, wherein said virus has an inactive UL4 gene, and wherein the foreign nucleic acid is located in the intergenic region of the virus between UL45 and UL46.

2. The DEV of claim 1, wherein at least 20% of the UL4 gene sequence is deleted.

3. The DEV of claim 1, wherein the foreign nucleic acid encodes an antigen.

4. The DEV of claim 3, wherein the antigen is a surface protein hemagglutinin (HA) of an avian influenza virus or an immunogenic fragment thereof.

5. The DEV of claim 3, wherein the foreign nucleic acid contains a transcriptional promoter.

6. The DEV of claim 1, wherein said DEV comprises a deleted UL4 gene and a foreign nucleic acid encoding a surface protein hemagglutinin (HA) of an avian influenza virus under control of a Pec promoter located in the intergenic region of the virus between UL45 and UL46.

7. A nucleic acid molecule comprising the genome of a DEV of claim 1.

8. A host cell comprising a DEV of claim 1 or a nucleic acid molecule comprising the genome of said DEV.

9. A composition comprising a DEV of claim 1 and a pharmaceutically or veterinary acceptable excipient or carrier.

10. The composition of claim 9, which further comprises an adjuvant.

11. A composition comprising a nucleic acid molecule comprising the genome of a DEV of claim 1 and a pharmaceutically or veterinary acceptable excipient or carrier.

12. The composition of claim 11, which further comprises an adjuvant.

13. A composition comprising a host cell according to claim 8 and a pharmaceutically or veterinary acceptable excipient or carrier.

14. The composition of claim 13, which further comprises an adjuvant.

* * * * *

UNITED STATES PATENT AND TRADEMARK OFFICE
CERTIFICATE OF CORRECTION

PATENT NO. : 10,717,967 B2
APPLICATION NO. : 16/251111
DATED : July 21, 2020
INVENTOR(S) : Saeki Yukari and Shuji Saitoh It is certified that error appears in the above-identified patent and that said Letters Patent is hereby corrected as shown below:

In the Specification

Column 21,
Line 18, "25 g," should read --25μF,--.

Column 24,
Line 16, "promoter/insertion gene/polyA", "Ba/VP2stc/SV40polyA" should read --Bac/VP2stc/SV40polyA--.

Signed and Sealed this
Tenth Day of November, 2020

Andrei Iancu
*Director of the United States Patent and Trademark Office*